(12) United States Patent
Lowe et al.

(10) Patent No.: US 8,227,254 B2
(45) Date of Patent: Jul. 24, 2012

(54) SENSOR MOLECULES INCORPORATING A BORONIC ACID SENSOR GROUP

(75) Inventors: Christopher Robin Lowe, Cambridge (GB); Felicity Kate Sartain, Cambridge (GB); Xiaoping Yang, Cambridge (GB)

(73) Assignee: Cambridge Enterprise Limited, Cambridge (GB)

( * ) Notice: Subject to any disclaimer, the term of this patent is extended or adjusted under 35 U.S.C. 154(b) by 462 days.

(21) Appl. No.: 11/814,965

(22) PCT Filed: Jan. 31, 2006

(86) PCT No.: PCT/GB2006/000317
§ 371 (c)(1),
(2), (4) Date: Aug. 23, 2007

(87) PCT Pub. No.: WO2006/079843
PCT Pub. Date: Aug. 3, 2006

(65) Prior Publication Data
US 2008/0160225 A1    Jul. 3, 2008

(30) Foreign Application Priority Data
Jan. 31, 2005  (GB) .................................. 0501944.3

(51) Int. Cl.
*G01N 33/00* (2006.01)
*C07C 233/29* (2006.01)
*C07C 63/66* (2006.01)
*C40B 40/04* (2006.01)
*C08F 30/06* (2006.01)
*B44F 1/00* (2006.01)
*G03F 7/00* (2006.01)
*G02B 5/32* (2006.01)

(52) U.S. Cl. .......... 436/129; 428/29; 564/207; 562/452; 506/15; 526/239; 430/2; 359/15

(58) Field of Classification Search ................. 436/129; 428/29; 564/207; 562/452; 506/15; 526/239; 430/2; 359/15
See application file for complete search history.

(56) References Cited

U.S. PATENT DOCUMENTS
6,180,288 B1    1/2001  Everhart et al.
(Continued)

FOREIGN PATENT DOCUMENTS
EP    0843173    5/1998
(Continued)

OTHER PUBLICATIONS

Imprinted Polymers as Protecting Groups for Regioselective Modification of Polyfunctional Substrates Cameron Alexander, Craig R. Smith, Michael J. Whitcombe, and Evgeny N. Vulfson J. Am. Chem Soc. 1999, 121, 6640-6651.*

(Continued)

*Primary Examiner* — Robert J Hill, Jr.
*Assistant Examiner* — Dwan A Gerido
(74) *Attorney, Agent, or Firm* — Michael Best & Friedrich LLP

(57) ABSTRACT

The present invention pertains to compounds and polymers which incorporate a boronic acid sensor group (SG) of the formula (I): wherein: J is independently $-CH_2-$ or $-CH_2CH_2-$; n is independently 0, 1, 2, or 3; and each $R^R$, if present, is independently a ring substituent; and wherein the ring attachment (i.e., where sensor group is attached) is via the 3-, 4-, 5-, or 6-ring position. Such compounds and polymers are useful in the selective chemical detection and/or quantitation of alpha-hydroxy carboxylic acids, such as lactic acid/lactate and malic acid/malate. The present invention also pertains to methods of preparing such compounds and polymers; methods and assays which employ these compounds and polymers; devices (e.g., holographic sensors) and kits for use in such methods and assays, etc.

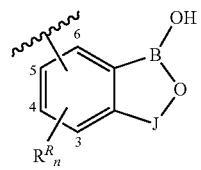

44 Claims, 5 Drawing Sheets

U.S. PATENT DOCUMENTS

| | | | |
|---|---|---|---|
| 6,198,869 | B1 | 3/2001 | Kraus et al. |
| 2003/0027240 | A1 | 2/2003 | Asher et al. |
| 2003/0224526 | A1* | 12/2003 | Lawrence et al. ............ 436/128 |

FOREIGN PATENT DOCUMENTS

| | | |
|---|---|---|
| WO | 95/26499 | 10/1995 |
| WO | 03/087799 | 10/2003 |
| WO | 03/087899 | 10/2003 |
| WO | 2004/081624 | 9/2004 |

OTHER PUBLICATIONS

Alexander, C. et al., "Imprinted polymers as protecting groups for regioselective modification of polyfunctional substrates," J. Amer. Chem. Soc. (1999) 121:6640-6651.

Cairns, J.F. et al., "Derivatives of 1,4-xylene-2,5-diboronic acid and 1,4-xylene-2-boronic acid," J. Org. Chem. (1964) 29(9):2810-2812.

Dowlut, M. et al., "An improved class of sugar-binding boronic acids, soluble and capable of complexing glycosides in neutral water," J. Amer. Chem. Soc. (2006) 128:4226-4227.

Kabilan, S. et al., "Holographic glucose sensors," Biosensors & Bioelectronics (2005) 20:1602-1610.

Lennarz, W.J. et al., "Arylboronic Acids. IV. Reactions of bronophthalide," J. Amer. Chem. Soc. (1960) 82:2172-2175.

Mayes et al., "A holographic sensor based on a rationally designed synthetic polymer," J. Mol. Recognition (1998) 11:168-174.

Sartain, F., "Design of a holographic lactate sensor," Ph.D. Thesis, Wolfson College, University of Cambridge (2005) 1-189.

Spooncer, R.C. et al., "A humidity sensor using a wavelength-dependent holographic filter with fibre optic links," Int. J. Optoelectronics (1992) 7:449-452.

Yamashita, H. et al., "Synthesis of terphenylboronic acid derivatives and recognition of anomers of 2-deoxyribofuranoside," Chem. Letters (1996) 537-538.

UK Search Report for GB 0501944.3.

International Search Report and Written Opinion of the International Searching Authority for PCT/GB2006/000317.

Alexeev, V.L. et al., "High ionic strength glucose-sensing photonic crystal," Anal. Chem. (2003) 75:2316-2323.

Alexeev, V.L. et al., "Photonic crystal glucose-sensing material for noninvasive monitoring of glucose in tear fluid," Clin. Chem. (2004) 50(12):2353-2360.

Asher, S.A. et al., "Photonic crystal carbohydrate sensors: low ionic strength sugar sensing," J. Am. Chem. Soc. (2003) 125:3322-3329.

Hedborg, E. et al., "Some studies of molecularly-imprinted polymer membranes in combination with field-effect devices," Sensors and Actuators A (1993) 37-38:796-799.

Kabilan, S. et al., "Glucose-sensitive holographic sensors," J. Mol. Recogn. (2004) 17:162-166.

Kriz, D. et al., "Molecular imprinting. New possibilities for sensor technology," Anal. Chemistry News & Features (1997) 345A-349A.

Lee, M-C. et al., "Glucose-sensitive holographic sensors for monitoring bacterial growth," Anal. Chem. (2004) 76:5748-5755.

Marshall, A.J. et al., "pH-sensitive holographic sensors," Anal. Chem. (2003) 75:4423-4431.

Piletsky, S.A. et al., "Sensors for low-weight organic molecules based on molecular imprinting technique," Sensors and Actuators B (1994) 18-19:629-631.

Yamamura, K. et al., "Guest selective molecular recognition by an octadecylsilyl monolayer covalently bound on an SnO2 electrode," J. Chem. Soc., Chem. Commun. (1988) 79-81.

Hariharan, P., "The Recording Medium," Chapter 5 of Basics of Holography, Cambridge University Press (2002) Table of contents and p. 46-49.

Hecht, E., Optics, 4th Edition, Addison Wesley, San Francisco (2002) content, preface and pp. 623-640.

Kasper, J.E. et al., The Complete Book of Holograms. How They Work and How to Make Them, John Wiley & Sons, Inc., New York (1987) contents, preface and chapter 1.

* cited by examiner

SENSOR MOLECULES INCORPORATING A BORONIC ACID SENSOR GROUP

CROSS REFERENCE TO RELATED APPLICATIONS

This application is a national stage filing under 35 U.S.C. 371 of International Application No. PCT/GB2006/000317, filed Jan. 31, 2006, which claims foreign priority benefits to United Kingdom (GB) patent application number 0501944.3 filed Jan. 31, 2005, the contents of which are incorporated herein by reference in their entirety.

TECHNICAL FIELD

The present invention pertains generally to the field of chemical analysis, and compounds and polymers useful in chemical detection and/or quantitation, and more specifically to compounds and polymers which incorporate a certain bicyclic boronic acid group which are useful in the highly selective chemical detection and/or quantitation of alpha-hydroxy carboxylic acids, such as lactic acid/lactate and malic acid/malate. The present invention also pertains to methods of preparing such compounds and polymers; methods and assays which employ these compounds and polymers; as well as devices (e.g., holographic sensors) and kits for use in such methods and assays.

BACKGROUND

A number of patents and publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiments.

Lowe et al., WO 03/087799 A1, published 23 Oct. 2003, describes methods for detecting analytes in a fluid with the aid of a holographic element. Example 1 therein describes a holographic element comprising a polyacrylamide polymer which incorporates vinylphenylboronic acid for the detection of glucose.

Lowe et al., WO 2004/081624 A1, published 23 Sep. 2004, describes certain phenyl boronic acids for use in holographic sensors for the detection of compounds bearing cis-diol moieties, such as glucose and tartarate. These phenyl boronic acids are described by the following formula, where X is a group which, via an electronic effect, promotes formation of a (more reactive) tetrahedral geometry about the boron atom, and Y is a spacer:

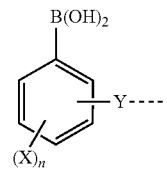

Lennarz et al., *Journal of American Chemical Society*, 1960, Vol. 82, pp. 2172-2175, describe the synthesis of the following azo-compound (3-hydroxy-4-(1-hydroxy-1,3-dihydro-benzo[c][1,2]oxaborol-6-ylazo)-naphthalene-2-carboxylic acid; "azo-BOB") (Compound VI therein, p. 2173). However, no teaching of its possible use is provided.

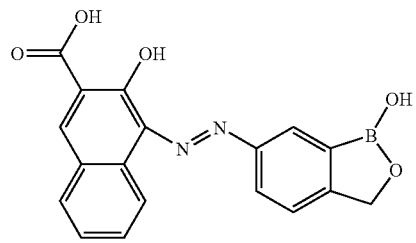

The following compounds are commercially available:

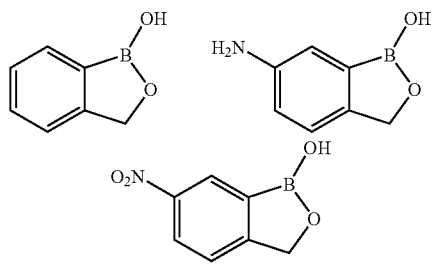

Lawrence et al., US 2003/0224526 A1, published 4 Dec. 2003, describe the optical sensors that employ a molecularly imprinted polymer containing a chromophore, in conjunction with a light source and a detector, to detect cortisol molecules with a relatively high degree of selectivity and sensitivity.

There is a need for materials and methods for the detection of alpha-hydroxy carboxylic acids, such as lactic acid/lactate and malic acid/malate, particularly the selective detection of such species, especially in the presence of glucose.

SUMMARY OF THE INVENTION

One aspect of the present invention pertains to sensor molecules (SMs) which incorporate a boronic acid sensor group (SG), as described herein, and which are useful, for example, in (selective) chemical detection and/or quantitation of alpha-hydroxy carboxylic acids, such as lactic acid/lactate.

Another aspect of the invention pertains to methods for the detection and/or quantitation of alpha-hydroxy carboxylic acids, such as lactic acid/lactate, which employ compounds or polymers which incorporate a sensor group (SG), as described herein.

Another aspect of the invention pertains to compounds and polymers which incorporate the sensor group (SG), as described herein, for use in methods for the detection and/or quantitation of alpha-hydroxy carboxylic acids, such as lactic acid/lactate.

Another aspect of the present invention pertains to reactive compounds which incorporate a sensor group (SG), as described herein, and which are useful, for example, in methods of introducing the sensor group into other molecules.

Another aspect of the present invention pertains to polymerisable reagents (e.g., monomers) which incorporate the sensor group (SG), as described herein, and which are useful, for example, in methods of introducing the sensor group into polymers.

Another aspect of the present invention pertains to polymers which incorporate the sensor group (SG), as described herein, and which are useful, for example, in (selective) chemical detection and/or quantitation of alpha-hydroxy carboxylic acids, such as lactic acid/lactate.

Other aspects of the invention will be apparent from this disclosure.

As will be appreciated by one of skill in the art, features and preferred embodiments of one aspect of the invention will also pertain to other aspects of the invention.

DETAILED DESCRIPTION OF THE INVENTION

Alpha-Hydroxy Carboxylic Acids

Many alpha-hydroxy carboxylic acids may be represented by the following general formula:

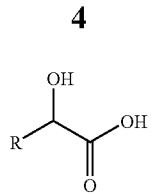

Two examples of such alpha-hydroxy carboxylic acids include lactic acid and malic acid:

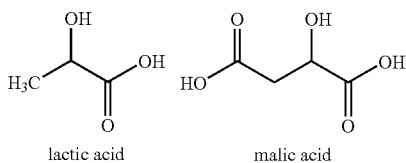

lactic acid      malic acid

Lactic acid has a pKa of 3.86, and at physiological pH, it exists in a charged anionic form as lactate. Similarly, the anionic form of malic acid is malate.

Compounds having a cis-diol group, such as glucose and tartarate, are known to bind to certain boronic acid compounds, including acrylamido-phenylboronic acids. This ligand-target binding has been exploited in methods for the detection and/or quantitation of glucose.

The inventors have discovered that, surprisingly and unexpectedly, lactate (which also has a cis-diol group) binds to 3- and 4-acrylamido-phenylboronic acid (3-APB, 4-APB), but does not bind to 2-acrylamido-phenylboronic acid (2-APB), at physiological pH. Without wishing to be bound by any particular theory, the inventors believe that this is due to the fact that the boron atom is in a tetrahedral conformation in 2-APB, but is predominantly in a trigonal conformation in 3-APB and 4-APB.

2-APB

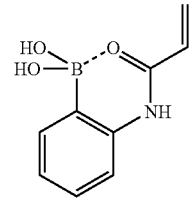

3-APB

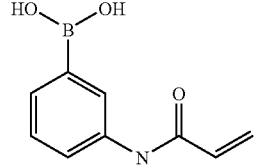

4-APB

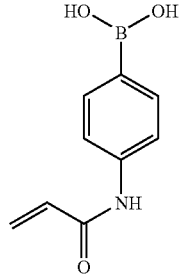

The inventors concluded that lactate binds to the boronic acid group, not via its diol (as would be expected by analogy with the binding of glucose to boronic acids), but instead by some other mechanism. Again, without wishing to be bound by any particular theory, the inventors believe that lactate binds to the boron atom via the negatively charged —C(=O)O⁻ group, and then rotates so that the alpha-hydroxy group also binds to the boron atom, as illustrated in the following scheme.

Scheme 1

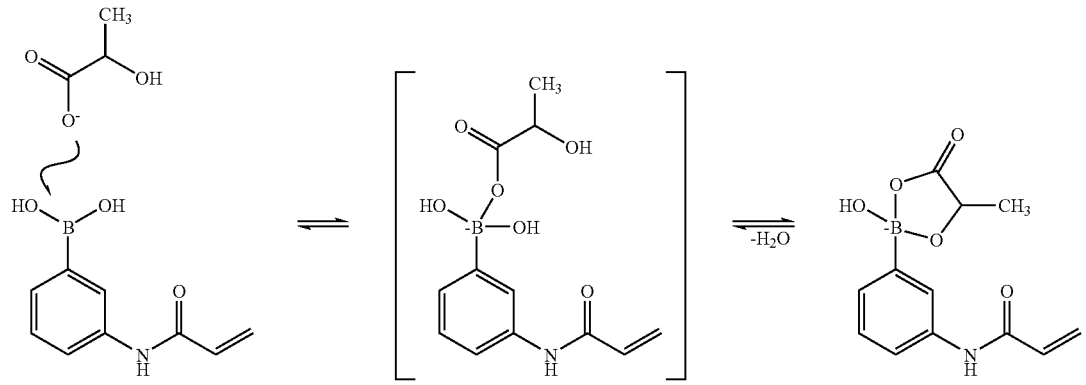

The inventors then discovered that one class of boronic acid compounds, represented by the following commercially available compound ((5-amino-2-hydroxymethylphenyl)boronic acid, HCl, dehydrate; also known as: 6-amino-1-hydroxy-2,1-benzooxaborolane, hydrochloride; referred to herein as 5A2HMPBA; available from Combi-Blocks Inc., San Diego, Calif., USA), do not bind to glucose, but do bind to alpha-hydroxy carboxylic acids, such as lactic acid/lactate, and in doing so, convert the boron atom to a tetrahedral conformation.

5A2HMPBA

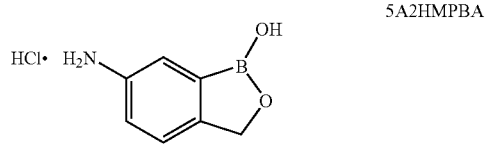

To demonstrate this effect, a stock solution of ~100 mg of 5A2HMPBA in 5 ml D$_2$O was prepared. $^{11}$B NMR spectra (128 MHz, JEOL instrument) were then recorded for three test solutions: (1) stock solution only, (2) stock solution plus 2.0 equivalents of glucose, and (3) stock solution plus 2.0 equivalents of lactate.

Figure 1:
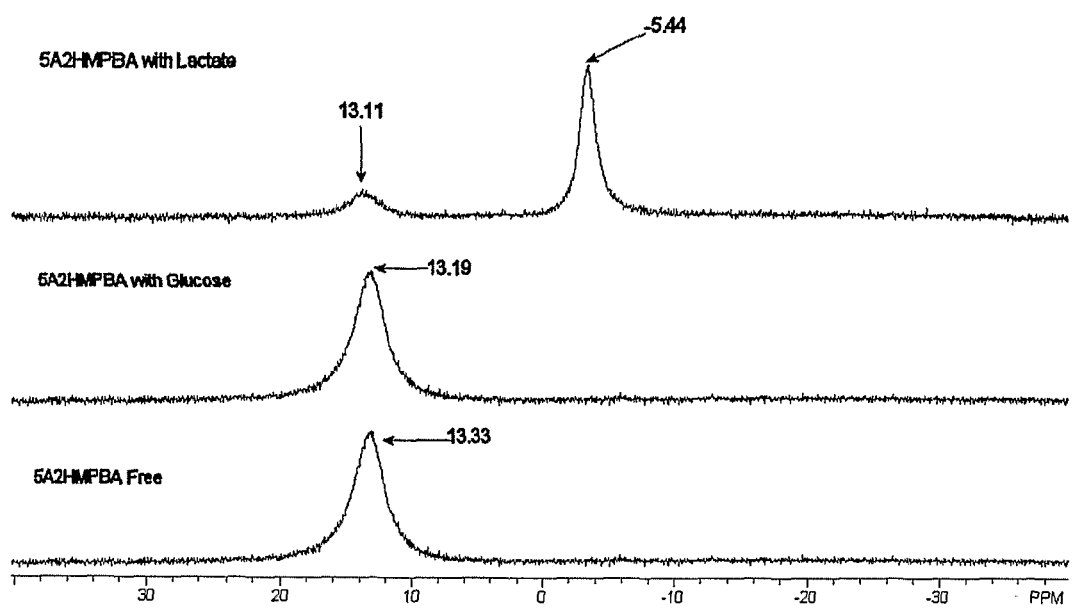
FIG. 1 shows the $^{11}$B NMR (128 MHz) spectra recorded for the boronic acid 5A2HMPBA with lactate, with glucose, and alone.

FIG. 1 shows the resulting $^{11}$B NMR spectra. The spectrum for 5A2HMPBA with lactate shows that the original trigonal boron species is greatly reduced, and a new tetrahedral boron species (5A2HMPBA bound to lactate) is formed in large proportions. Conversely, the spectrum for glucose shows that the trigonal boron species is largely unaffected by the presence of glucose, showing that glucose does not bind to 5A2HMPBA.

The inventors then developed compounds and polymers bearing particular boronic acid groups (similar to the group in 5A2HMPBA and denoted herein as "sensor groups") for use in the (selective) chemical detection and/or quantitation of alpha-hydroxy carboxylic acids, such as lactic acid/lactate.

The Sensor Group (SG)

The sensor group (SG) referred to herein is a group of the formula:

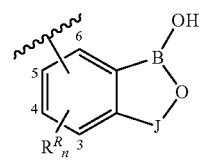

wherein:
J is independently —CH$_2$— or —CH$_2$CH$_2$—;
n is independently 0, 1, 2, or 3; and
each R$^R$, if present, is independently a ring substituent;
and wherein the ring attachment (i.e., where sensor group is attached) is via the 3-, 4-, 5-, or 6-ring position.
In one embodiment, J is independently —CH$_2$—.
In one embodiment, J is independently —CH$_2$CH$_2$—.
In one embodiment, n is independently 0, 1, 2, or 3.
In one embodiment, n is independently 1, 2, or 3.
In one embodiment, n is independently 0, 1, or 2.
In one embodiment, n is independently 1 or 2.
In one embodiment, n is independently 0 or 1.
In one embodiment, n is independently 0.
In one embodiment, n is independently 1.
In one embodiment, n is independently 2.
In one embodiment, n is independently 3.
In one embodiment, the ring attachment is via the 3, 4-, 5-, or 6-ring position.
In one embodiment, the ring attachment is via the 3-, 4-, or 5-ring position.
In one embodiment, the ring attachment is via the 4- or 5-ring position.
In one embodiment, the ring attachment is via the 4-ring position.
In one embodiment, the ring attachment is via the 5-ring position.
In one embodiment, each R$^R$ is independently selected from:

(1) $C_{1-6}$alkoxy (—OR, where R is $C_{1-7}$alkyl, e.g., -Me, -Et, -nPr, -iPr, -nBu, -iBu, -tBu);
(2) nitro (—NO$_2$);
(3) acyl (—C(=O)R), including $C_{1-7}$alkyl-acyl (—C(=O)R, where R is $C_{1-7}$alkyl, e.g., -Me, -Et, -nPr, -iPr, -nBu, -iBu, -tBu); $C_{5-10}$aryl-acyl (—C(=O)R, where R is $C_{5-10}$aryl, e.g., phenyl, pyridyl, pyrrolyl, furanyl, thiofuranyl); $C_{5-10}$aryl-$C_{1-7}$alkyl-acyl (—C(=O)R, where R is $C_{5-10}$aryl-$C_{1-7}$alkyl, e.g., benzyl);
(4) hydroxy (—OH);
(5) carboxylic acid (—COOH);
(6) halogen (—F, —Cl, —Br, —I);
(7) cyano (—CN).

In one embodiment, each $R^R$ is independently selected from (1) through (5) above.

All plausible combinations of the embodiments described above are explicitly disclosed herein, as if each combination was explicitly recited.

In one embodiment, J is —CH$_2$— and n is 0, and the sensor group (SG) is a group of the following formula, wherein the ring attachment is via the 3-, 4-, 5-, or 6-ring position (or as defined above):

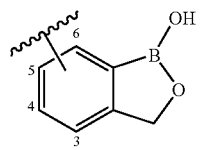

In one embodiment, J is —CH$_2$—, n is 0, and the ring attachment is via the 5-ring position, and the sensor group (SG) is a group of the following formula (which may be referred to as 3H-benzo[c][1,2]oxaborol-1-ol-5-yl):

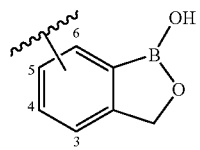

Sensor Group Reagents (SGRs)

Sensor group reagents (SGRs) which incorporate (i.e., by way of covalent bonds) a sensor group (SG) and which bear one or more reactive functional groups, may be used (e.g., in methods of chemical synthesis) to introduce a sensor group into other molecules.

In one embodiment, the sensor group reagent (SGR) is a compound of the following formula:

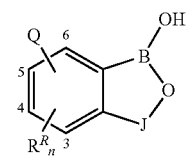

wherein:
J, n, each $R^R$, if present, and the ring attachment are as defined above for sensor groups; and
Q is, or incorporates, a reactive functional group.

The reactive functional group, Q, is a group that forms a covalent bond or linkage upon chemical reaction with another reactive functional group, for example, on the molecule into which the sensor group is to be incorporated.

In one embodiment, Q is selected from groups which are, or which incorporate:
(1) —NR$^1$R$^2$, wherein each of R$^1$ and R$^2$ is independently —H, $C_{1-7}$alkyl, $C_{5-20}$aryl (which includes $C_{6-10}$carboaryl and $C_{5-10}$heteroaryl), $C_{5-20}$aryl-$C_{1-7}$alkyl, or $C_{3-10}$heterocyclyl; or R$^1$ and R$^2$ taken together with the nitrogen atom to which they are attached form a ring having from 3 to 7 ring atoms.
(2) hydroxy (—OH);
(3) carboxylic acid (—COOH);
(4) ester (—COOR, where R is $C_{1-7}$alkyl, $C_{5-20}$aryl (which includes $C_{6-10}$carboaryl and $C_{5-10}$heteroaryl), $C_{5-20}$aryl-$C_{1-7}$alkyl, or $C_{3-10}$heterocyclyl, and is optionally substituted, for example, with one or more groups as defined for $R^R$.

In one embodiment, Q is selected from groups which are as defined above in (1) through (4).

In one embodiment, Q is selected from groups which are, or which incorporate:
(1) —NH$_2$, —NHMe, —NHEt, —NHPh, —NH-pyridyl, piperidino, piperazino;
(2) —OH;
(3) —COOH;
(4) —COOMe, —COOEt, —COO(tBu), —COOPh, —COOCH$_2$Ph.

In one embodiment, Q is —NH$_2$.

For example, the following 5-amino compound is commercially available:

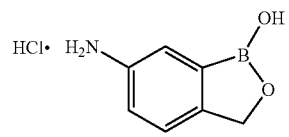

Other suitable sensor group reagents (SGRs) may be prepared using well known methods. For example, a 3-amino compound may be prepared using the method illustrated in the following scheme.

Scheme 2

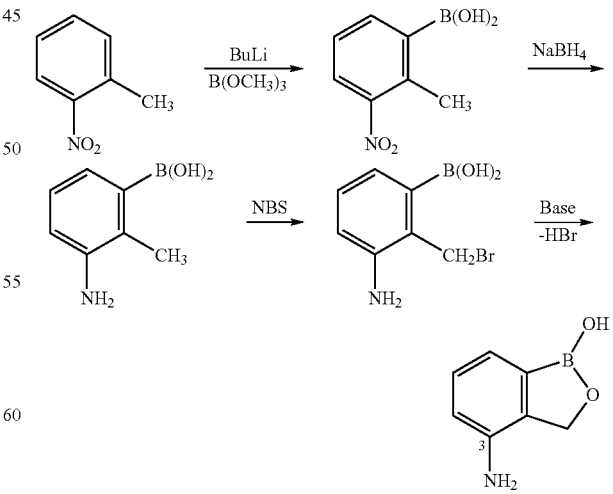

Similarly, a 4-amino compound and a 6-amino compound may be prepared by analogous methods using corresponding starting materials, as illustrated in the following scheme.

Scheme 3

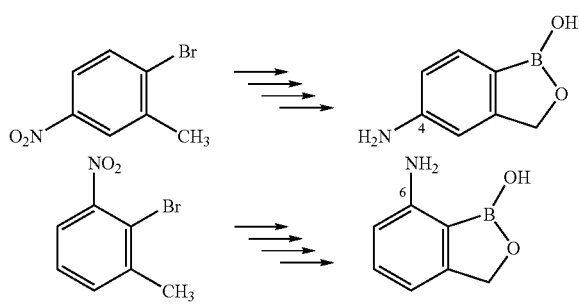

Other sensor group reagents (SGRs) that incorporate the sensor group may also be prepared using well known methods.

As discussed above, one aspect of the present invention pertains to novel sensor group reagents (SGRs) that incorporate a sensor group (SG).

In one embodiment (of the sensor group reagent, per se), Q is as defined above, with the proviso that the compound is not 5A2HMPBA.

In one embodiment (of the sensor group reagent, per se), Q is as defined above, with the proviso that Q is not —NH$_2$ or —NO$_2$.

In one embodiment (of the sensor group reagent, per se), Q is selected from groups which are, or which incorporate, as defined above in (2) through (4).

In one embodiment (of the sensor group reagent, per se), Q is selected from groups which are as defined above in (2) through (4).

Polymerisable Sensor Group Reagents (PSGRs)

As discussed above, one aspect of the present invention pertains to polymerisable sensor group reagents (PSGRs) (e.g., monomers, pre-polymers) that incorporate a sensor group (SG).

Such reagents may be used (e.g., in methods of chemical synthesis) to introduce a sensor group into polymers. For example, polymers incorporating a sensor group (SG) may be prepared by employing a monomer (or pre-polymer) which incorporates a sensor group (SG), and which bears one or more polymerisable groups.

In one embodiment, the polymerisable sensor group reagent (PSGR) is a compound of the following formula:

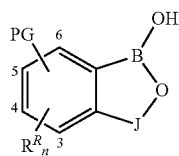

wherein:
J, n, each R$^R$, if present, and the ring attachment are as defined above for sensor groups; and
PG is, or incorporates, a polymerisable group.

The polymerisable group, PG, is a group that, in a polymerisation reaction, forms a covalent bond or linkage upon chemical reaction with another polymerisable group, for example, on another monomer, to yield (ultimately) a polymer into which the sensor group is incorporated.

In one embodiment, the polymerisable group (PG) is, or incorporates, a non-vinyl polymerisable group.

In one embodiment, the polymerisable group (PG) is, or incorporates:

(1) a C$_{1-6}$alkylene oxide, such as ethylene oxide, propylene oxide;
(2) a C$_{1-6}$alkylene diol, such as ethylene glycol;
(3) a C$_{1-4}$aldehyde, such as formaldehyde and acetaldehyde;
(4) a lactone, such as beta-propiolactone;
(5) a hydroxy-C$_{1-12}$alkanoic acid, such as 10-hydroxydecanoic acid;
(6) a C$_{5-20}$aryl-di-carboxylic acid, such as terephthalic acid;
(7) a diol, such as bisphenol A;
(8) a diamine, such as piperazine and 1,6-diaminohexane;
(9) a lactam, such as caprolactam;
(10) an amino-C$_{1-12}$alkanoic acid, such as 11-aminoundecanoic acid;
(11) a C$_{5-20}$aryl-di(acid halide), such as terephthaloyl chloride;
(12) a C$_{5-20}$aryl-diamine, such as meta-phenylenediamine; or
(13) a diisocyanate, such as 1,6-diisocyanto-hexane.

For example, in one embodiment, the polymerisable group (PG) is the following group (an example of "a group which is, or incorporates ethylene oxide"):

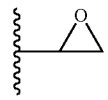

In one embodiment, the polymerisable group (PG) is, or incorporates, a polymerisable vinyl group (i.e., a group suitable for vinyl polymerisation).

The term "vinyl group", as used herein, pertains groups of the formula >C=C<, and so includes both the simple vinyl group (—CH=CH$_2$) and substituted forms thereof, including, e.g., —CH=CH$_2$, —CH=CHR, —CH=CR$_2$, —CR=CH$_2$, —CR=CHR, —CR=CR$_2$.

In one embodiment, the polymerisable group (PG) is, or incorporates:

(1) a C$_{1-6}$alkenylene, such as ethylene, propylene, butylene, isobutylene, isoprene;
(2) a C$_{5-10}$aryl-C$_{1-6}$alkenylene, such as styrene;
(3) acrylic acid;
(4) a C$_{1-4}$alkyl substituted acrylic acid, such as methacrylic acid;
(5) a C$_{1-4}$alkyl acrylate, such as methyl acrylate;
(6) a C$_{1-4}$alkyl C$_{1-4}$alkyl-substituted acrylate, such as methyl methacrylate;
(7) a hydroxy-C$_{1-4}$alkyl acrylate, such as hydroxyethyl acrylate;
(8) a hydroxy-C$_{1-4}$alkyl C$_{1-4}$alkyl-substituted acrylate, such as hydroxyethyl methacrylate;
(9) acrylamide;
(10) a C$_{1-4}$alkyl substituted acrylamide, such as methacrylamide;
(11) an N—C$_{1-4}$alkyl- or N,N-di-C$_{1-4}$alkyl-substituted acrylamide, such as N-methyl-acrylamide;
(12) an N—C$_{1-4}$alkyl- or N,N-di-C$_{1-4}$alkyl-substituted C$_{1-4}$alkyl substituted acrylamide, such as N-methyl-methacrylamide;
(13) a vinyl ester, such as vinyl acetate;
(14) a C$_{1-4}$alkyl substituted vinyl ester, such as methylvinyl acetate;
(15) acrylonitrile;
(16) a C$_{1-4}$alkyl substituted acrylonitrile, such as methacrylonitrile;
(17) vinyl chloride; or

(18) a $C_{1-4}$alkyl substituted vinyl chloride, such as methylvinyl chloride.

For example, in one embodiment, the polymerisable group (PG) is the following group (an example of "a group which is, or incorporates acrylamide"):

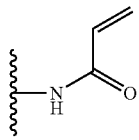

In one embodiment, the polymerisable group (PG) is, or incorporates a group as defined in one of (3) through (12) above.

In one embodiment, the polymerisable group (PG) is, or incorporates a group as defined in one of (9) through (12) above. (For example, linked via the nitrogen atom of the amide.)

In one embodiment, the polymerisable group (PG) is, or incorporates a group a group as defined in (9) above (e.g., $H_2C=CH—C(=O)NH—$).

Thus, in one embodiment, the polymerisable sensor group reagent (PSGR) is a compound of the following formula:

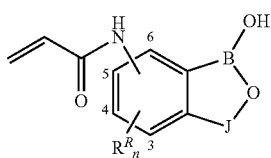

wherein:
J, n, each $R^R$, if present, and the ring attachment are as defined above for sensor groups.

An example of a method for the preparation of one such reagent is illustrated in the following scheme.

Scheme 4

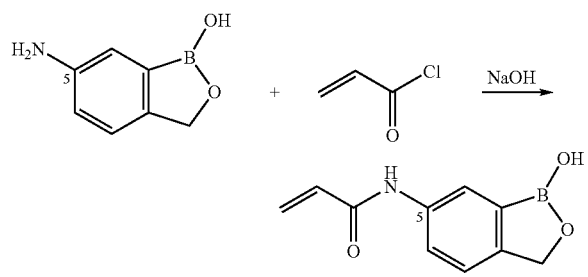

Other polymerisable sensor group reagents (PSGRs) that incorporate the sensor group may also be prepared using well known methods.

Sensor Polymers (SPs)

As discussed above, one aspect of the present invention pertains to sensor polymers (SPs) which incorporate a sensor group (SG).

The sensor polymer (SP) may incorporate one, or one or more, or two or more sensor groups (SGs), which may be the same or different, but are preferably the same.

The sensor polymer (SP) may incorporate a (e.g., water) soluble polymeric group, and/or may be a (e.g., water) soluble polymer.

The sensor polymer (SP) may be, or form, or form part of, a support, for example, a solid or gel support, for example, a film or sheet or layer (e.g., a polymeric film), or a particle or bead (e.g., a polymeric bead, nanoparticle, etc.), or other support matrix.

In one embodiment, the sensor polymer (SP) is a non-vinyl polymer or a vinyl polymer.

In one embodiment, the sensor polymer (SP) is a non-vinyl polymer.

In one embodiment, the sensor polymer (SP) is selected from: polyethers, polyesters, polycarbonates, polyamides, polyureas, polyurethanes, and copolymers thereof.

In one embodiment, the sensor polymer (SP) is a vinyl polymer.

In one embodiment, the sensor polymer (SP) is selected from:

(1) poly(alkylene)s, such as polyethylene, polypropylene, polybutylene, polyisobutylene, polyisoprene;
(2) poly(arylalklene)s, such as polystyrene;
(3) poly(acrylic acid);
(4) poly($C_{1-4}$alkyl substituted acrylic acid)s, such as poly(methacrylic acid);
(5) poly($C_{1-4}$alkyl acrylate)s, such as poly(methyl acrylate);
(6) poly($C_{1-4}$alkyl $C_{1-4}$alkyl-substituted acrylate)s, such as poly(methyl methacrylate);
(7) poly(hydroxy-$C_{1-4}$alkyl acrylate)s, such as poly(hydroxyethyl acrylate);
(8) poly(hydroxy-$C_{1-4}$alkyl $C_{1-4}$alkyl-substituted acrylate)s, such as poly(hydroxyethyl methacrylate);
(9) poly(acrylamide);
(10) poly($C_{1-4}$alkyl substituted acrylamide)s, such as poly(methacrylamide);
(11) poly(N—$C_{1-4}$alkyl- or N,N-di-$C_{1-4}$alkyl-substituted acrylamide)s, such as poly(N-methyl-acrylamide);
(12) poly(N—$C_{1-4}$alkyl- or N,N-di-$C_{1-4}$alkyl-substituted $C_{1-4}$alkyl substituted acrylamide)s, such as poly(N-methyl-methacrylamide);
(13) poly(vinyl esters), such as poly(vinyl acetate);
(14) poly($C_{1-4}$alkyl substituted vinyl ester)s, such as poly(methylvinyl acetate);
(15) poly(acrylonitrile);
(16) poly($C_{1-4}$alkyl substituted acrylonitrile)s, such as poly(methacrylonitrile);
(17) poly(vinyl chloride);
(18) poly($C_{1-4}$alkyl substituted vinyl chloride)s, such as poly(methylvinyl chloride); and copolymers thereof.

In one embodiment, the polymer is selected from: gelatin, K-carageenan, agar, agarose, polyvinyl alcohol (PVA), sol-gels (as broadly classified), hydro-gels (as broadly classified), polysaccharides, proteins, oligonucleotides, RNA, DNA, cellulose, cellulose acetate, siloxanes, and polyimides.

In one embodiment, the sensor polymer (SP) is a compound of the following formula:

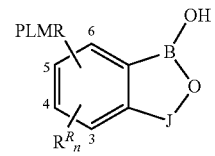

wherein:
J, n, each $R^R$, if present, and the ring attachment are as defined above for sensor groups; and
PLMR is a polymeric group.

In one embodiment, PLMR is a non-vinyl polymeric group derived from a non-vinyl polymer (e.g., polyethers, polyesters, etc., as above).

In one embodiment, PLMR is a vinyl polymeric group derived from a vinyl-polymer (e.g., poly(alkylene)s, poly(arylalkylene)s, etc., as above).

The polymeric group, PLMR, may be linked, for example, via one of its termini or via an internal (non-terminal) point. In one example, PLMR may be derived from a polyether (e.g., polyethylene glycol, $H(OCH_2CH_2)_nOH$), and the sensor group (SG) may be present as a terminal ether group (e.g., $H(OCH_2CH_2)_nOSG$). In another example, PLMR may be derived from a polyacrylamide (e.g., $H[CH(CONH_2)CH_2]_nH$), and the sensor group(s) may be present as one or more N-substituents.

In one embodiment, the sensor polymer (SP) comprises a monomer unit bearing a sensor group (SG).

In one embodiment, the sensor group (SG) is attached to the monomer unit directly or via a linker group (L).

Examples of linker groups (L) include:
(1) $C_{1-6}$alkylene (e.g., —$CH_2$—, —$CH_2CH_2$—, —$CH_2CH_2CH_2$—, —$CH(CH_3)CH_2$—);
(2) oxy (i.e., —O—);
(3) amino and substituted amino (e.g., —NH—, —NR—, where R is, e.g., $C_{1-6}$alkyl);
(4) amino acyl and acyl amino and N-substituted amino acyl and acyl amino (e.g., —NHC(=O)—, —C(=O)NH—, —NRC(=O)—, —C(=O)NR—, R is e.g., $C_{1-6}$alkyl);
(5) esters and reverse esters (e.g., —OC(=O)— and —C(=O)O—);
(6) ureas substituted amino (e.g., —NHC(=O)NH—, —NRC(=O)NR—, where R is, e.g., $C_{1-6}$alkyl);
(7) carbamates and reverse carbamates and N-substituted carbamates and reverse carbamates (e.g., —O—C(=O)NH—, —NH—C(=O)—O—, —O—C(=O)NR—, —NR—C(=O)—O—, where R is, e.g., $C_{1-6}$alkyl); and
(8) combinations thereof.

Preferred (8) combinations include combinations of one or more (1) $C_{1-6}$alkylene groups with one or more (e.g., two) of the groups as defined in (2) to (7).

Examples of such combinations include the following:
(8-1) $C_{1-6}$alkylene-oxy (e.g., —$CH_2$—O—, —$CH_2CH_2$—O—, —$CH_2CH_2CH_2$—O—, —$CH(CH_3)CH_2$—O—);
(8-2) oxy-$C_{1-6}$alkylene (e.g., —O—$CH_2$—, —O—$CH_2CH_2$—, —O—$CH_2CH_2CH_2$—, —O—$CH(CH_3)CH_2$—);
(8-3) oxy-$C_{1-6}$alkylene-oxy (e.g., —O—$CH_2$—O—, —O—$CH_2CH_2$—O—);
(8-4) amino- and substituted amino-$C_{1-6}$alkylene (e.g., —NH—$CH_2$—, —NR—$CH_2$—, where R is, e.g., $C_{1-6}$alkyl);
(8-5) $C_{1-6}$alkylene-amino and substituted amino (e.g., —$CH_2$—NH—, —$CH_2$—NR—, where R is, e.g., $C_{1-6}$alkyl);
(8-6) $C_{1-6}$alkylene-amino- and substituted amino-$C_{1-6}$alkylene (e.g., —$CH_2$—NH—$CH_2$—, —$CH_2$—NR—$CH_2$—, where R is, e.g., $C_{1-6}$alkyl).

In one embodiment, the monomer unit is derived from a non-vinyl monomer.

In one embodiment, the monomer unit is derived from a non-vinyl monomer selected from: those that give rise to polyethers (e.g., $C_{1-6}$alkylene oxides, such as ethylene oxide, propylene oxide; $C_{1-6}$alkylene-diols, such as ethylene glycol; $C_{1-4}$aldehydes, such as formaldehyde and acetaldehyde); those that give rise to polyesters (e.g., lactones, such as beta-propiolactone; hydroxy-$C_{1-12}$alkanoic acids, such as 10-hydroxydecanoic acid; $C_{5-20}$aryl-di-carboxylic acids, such as terephthalic acid; $C_{1-6}$alkylene-diols, such as ethylene glycol); those that give rise to polycarbonates (e.g., diols, such as bisphenol A); those that give rise to polyamides (e.g., lactams, such as caprolactam; amino-$C_{1-12}$alkanoic acids, such as 11-aminoundecanoic acid; $C_{5-20}$aryl-di(acid halide)s, such as terephthaloyl chroide; $C_{5-20}$aryl-diamines, such as meta-phenylenediamine); those that give rise to polyureas (e.g., diamines, such as piperazine and 1,6-diaminohexane; $C_{5-20}$aryl-diamines, such as meta-phenylenediamine); those that give rise to polyurethanes (e.g., diols, diamines, diisocyanates such as 1,6-diisocyanto-hexane).

In one embodiment, the monomer unit is derived from a vinyl monomer. (A vinyl monomer is a monomer that incorporates a vinyl group.)

In one embodiment, the monomer unit is derived from a vinyl monomer selected from:
(1) $C_{1-6}$alkenylene, such as ethylene, propylene, butylene, isobutylene, isoprene;
(2) $C_{5-10}$aryl-$C_{1-6}$alkenylene, such as styrene;
(3) acrylic acid;
(4) $C_{1-4}$alkyl substituted acrylic acid, such as methacrylic acid;
(5) $C_{1-4}$alkyl acrylate, such as methyl acrylate;
(6) $C_{1-4}$alkyl $C_{1-4}$alkyl-substituted acrylate, such as methyl methacrylate;
(7) hydroxy-$C_{1-4}$alkyl acrylate, such as hydroxyethyl acrylate;
(8) hydroxy-$C_{1-4}$alkyl $C_{1-4}$alkyl-substituted acrylate, such as hydroxyethyl methacrylate;
(9) acrylamide;
(10) $C_{1-4}$alkyl substituted acrylamide, such as methacrylamide;
(11) N—$C_{1-4}$alkyl- or N,N-di-$C_{1-4}$alkyl-substituted acrylamide, such as N-methyl-acrylamide;
(12) N—$C_{1-4}$alkyl- or N,N-di-$C_{1-4}$alkyl-substituted $C_{1-4}$alkyl substituted acrylamide, such as N-methyl-methacrylamide;
(13) vinyl ester, such as vinyl acetate;
(14) $C_{1-4}$alkyl substituted vinyl esters, such as methylvinyl acetate;
(15) acrylonitrile;
(16) $C_{1-4}$alkyl substituted acrylonitrile, such as methacrylonitrile;
(17) vinyl chloride;
(18) $C_{1-4}$alkyl substituted vinyl chloride, such as methylvinyl chloride.

In one embodiment, the monomer unit is derived from a vinyl monomer selected from groups as defined in (3) through (12) above.

In one embodiment, the monomer unit is derived from a vinyl monomer selected from groups as defined in (9) through (12) above.

In one embodiment, the monomer unit is derived from a vinyl monomer selected from groups as defined in (9) and (10) above.

In one embodiment, the monomer unit is derived from a vinyl monomer selected from groups as defined in (9) above.

In one embodiment, the monomer unit is derived from a vinyl monomer (e.g., as described above), and a sensor group (SG) is attached, for example, directly or via a linker group (L), to one of the carbon atoms of the vinyl group.

For example, in one embodiment, the monomer unit is derived from N-substituted acrylamide or N-substituted $C_{1-4}$alkyl substituted acrylamide (e.g., N-substituted methacrylamide) which bears a sensor group (SG) as an N-substituent, for example, as shown below:

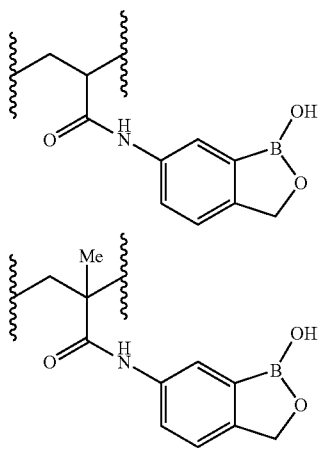

An example of such an embodiment is illustrated in the following scheme. Here, a poly(acrylamide) polymer is prepared from both acrylamide and N-(SG)-acrylamide.

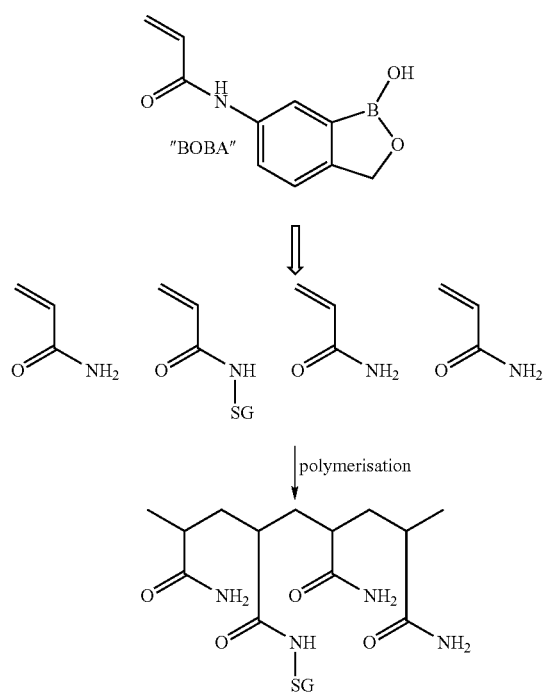

Scheme 4

In one embodiment, the ratio of the number of sensor groups (SG) to the number of monomer units (e.g., acrylamide monomer units) (i.e., the molar ratio) is from about 0.01 (i.e., 1 mol %) to about 0.4 (i.e., 40 mol %). In one embodiment, the lower limit is about 0.02 (i.e., 2 mol %); about 0.05 (i.e., 5 mol %). In one embodiment, the upper limit is about 0.2 (i.e., 20 mol %); about 0.15 (i.e., 15 mol %). All combinations of lower and upper limits are included as if they were explicitly recited. In one embodiment, the ratio is about 0.1 (i.e., 10 mol %).

In one embodiment, the sensor polymer (SP) has an average molecular weight of about 500 to about 100,000 g/mol. In one embodiment, the lower limit is about 1,000 g/mol; about 2,000 g/mol; about 3,000 g/mol; about 5,000 g/mol. In one embodiment, the upper limit is about 50,000 g/mol; about 30,000 g/mol; about 20,000 g/mol; about 10,000 g/mol. All combinations of lower and upper limits are included as if they were explicitly recited.

In one embodiment, the sensor groups (SGs) account for from about 1 to about 50% of the weight of the polymer (SP). In one embodiment, the lower limit is about 2%; about 5%; about 10%; about 15%. In one embodiment, the upper limit is about 45%; about 40%; about 35%; about 30%. All combinations of lower and upper limits are included as if they were explicitly recited.

An acrylamide monomer unit ($-CH_2-CH(CONH_2)-$) has a molecular weight of about 71.08 g/mol. A preferred sensor group (where J is $-CH_2-$ and n is 0) has a molecular weight of about 132.93 g/mol. An acrylamide monomer unit bearing such a sensor group has a molecular weight of about 203.00 g/mol. Consequently, for a poly(acrylamide) polymer where the molar ratio referred to above is 0.1, sensor groups account for about 24% of the total weight of the polymer. Such a polymer, with 100 acrylamide monomer units, has a molecular weight of about 8427 g/mol.

In one embodiment, the poly(acrylamide) polymer or copolymer incorporates a suitable cross-linking reagent, for example, N,N'-methylenebis(acrylamide) (i.e., $H_2C=CH-C(=O)NH-CH_2-NHC(=O)-CH=CH_2$).

In one embodiment, the ratio of the number of N,N'-methylenebis(acrylamide) monomer units to the number to acrylamide monomer units (i.e., the molar ratio) is from about 0.005 (i.e., 0.5 mol %) to about 0.1 (i.e., 10 mol %). In one embodiment, the lower limit is about 0.01 (i.e., 1 mol %); about 0.02 (i.e., 2 mol %). In one embodiment, the upper limit is about 0.05 (i.e., 5 mol %). All combinations of lower and upper limits are included as if they were explicitly recited. In one embodiment, the ratio is about 0.02 (i.e., 2 mol %).

In one embodiment, the sensor polymer (SR) is prepared by polymerisation of monomers which include a polymerisable sensor group reagent (PSGR) as described herein.

For example, a suitable polymer may be prepared by polymerisation of (for example, a mixture of) acrylamide and BOBA, or optionally, acrylamide, BOBA, and N,N'-methylenebis(acrylamide).

For example, a suitable polymer may be prepared by polymerisation of (for example, a mixture of):

(a) acrylamide (92.59 mg, 71.08 g/mol, 1.30 mmol, 88.17 mol %);

(b) N,N'-methylenebis(acrylamide) (3.93 mg, 154.17 g μmol, 0.0255 mmol, 1.73 mol %);

(c) BOBA (30.28 mg, 203.0 g/mol, 0.149 mmol, 10.1 mol %).

Other polymers that incorporate the sensor group may also be prepared using well known methods.

Sensor Molecules (SMs)

Sensor molecules (SMs) which incorporate a sensor group (SG) are useful, for example, in (selective) chemical detection and/or quantitation of alpha-hydroxy carboxylic acids, such as lactic acid/lactate.

In one embodiment, the sensor molecule (SM) is a compound or polymer that incorporates a sensor group (SG) as described herein.

In one embodiment, the sensor molecule (SM) is a compound or polymer of the following formula:

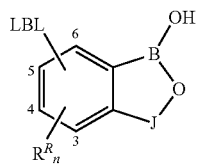

wherein:
J, n, each $R^R$, if present, and the ring attachment are as defined above for sensor groups; and
LBL is, or incorporates, a detectable label.

In one embodiment, the detectable label, LBL, is non-polymeric.

In one embodiment, the detectable label, LBL, is polymeric.

In one embodiment, the sensor molecule (SM) is non-polymeric.

In one embodiment, the sensor molecule (SM) is polymeric.

In one embodiment, the sensor molecule (SM) incorporates a (e.g., water) soluble polymeric group (linked, for example, via LBL or one or more $R^R$ groups, if present; for example, LBL or one or more $R^R$ groups, if present, is or incorporates a (e.g., water) soluble polymeric group).

In one embodiment, the sensor molecule (SM) is covalently attached or tethered (e.g., via LBL or one or more $R^R$ groups, if present) to a support, for example, a solid or gel support, for example, a film or sheet or layer (e.g., a polymeric film), or a particle or bead (e.g., a polymeric bead, a nanoparticle, etc.), or other support matrix. In one embodiment, the sensor molecule (SM) is not so attached or tethered, and is "free."

The detectable label, LBL, is a group which, in combination with the sensor group (SG), yields a sensor molecule (SM) that has physical and/or chemical properties that are suitable for detection and/or quantitation, for example, a sensor molecule (SM) that has physical and/or chemical properties that undergo readily detectable changes upon binding with alpha-hydroxy carboxylic acids, such as lactic acid/lactate.

In one embodiment, the chemical and/or physical property is colour.

In one embodiment, the chemical and/or physical property is absorbance or transmittance or reflectance or refractance at one or more UV or visible wavelengths.

In one embodiment, the chemical and/or physical property is fluorescence.

In one embodiment, the chemical and/or physical property is electrochemical response.

In one embodiment, the chemical and/or physical property is the chemical shift of an NMR resonance (e.g., of the boron atom of the sensor group).

In one embodiment, the chemical and/or physical property is the field strength of an electron spin resonance peak.

In one example, the sensor molecule (SM) undergoes a colour change upon binding with alpha-hydroxy carboxylic acids, such as lactic acid/lactate, and acts, for example, as a dye. For example, the sensor molecule (SM) may be or incorporate (e.g., as LBL) a chromophore. Such sensor molecules (SM) are useful in colour-based detection and/or quantitation methods (e.g., spectrophotometric analysis, colorimetric analysis).

In another example, the sensor molecule (SM) undergoes a change upon binding with alpha-hydroxy carboxylic acids, such as lactic acid/lactate, that is detectable using, for example, fluorescence methods. For example, the sensor molecule (SM) may be or incorporate (e.g., as LBL) a fluorescence label (a fluorophore).

In another example, the sensor molecule (SM) undergoes a change upon binding with alpha-hydroxy carboxylic acids, such as lactic acid/lactate, that is detectable using, for example, electrochemical methods. For example, the sensor molecule (SM) may be or incorporate (e.g., as LBL) a redox label.

In another example, the sensor molecule (SM) undergoes a change upon binding with alpha-hydroxy carboxylic acids, such as lactic acid/lactate, that is detectable using, for example, nuclear magnetic resonance (NMR), ultraviolet or visible or infrared spectroscopy, or electron spin resonance.

In one embodiment, the detectable label, LBL, is a chromophore (e.g., a dye group).

In one embodiment, the detectable label, LBL, is, or incorporates an azide (i.e., —N=N—R, where R is an aromatic organic group, for example, an aromatic organic group comprising 5 to 30 atoms selected from C, N, O, S, F, Cl, Br, and I).

In one embodiment, the detectable label, LBL, is, or incorporates an aryl azide of the formula —N=N—Ar, wherein Ar is $C_{5-20}$aryl or $C_{1-7}$alkyl-$C_{5-20}$aryl (where $C_{5-20}$aryl includes both $C_{6-20}$carboaryl and $C_{5-20}$heteroaryl) and is optionally substituted with one or more (e.g., 1, 2, 3, 4, etc.) groups selected from:

(1) hydroxy (—OH);

(2) carboxylic acid (—COOH);

(3) nitro (—NO$_2$);

(4) $C_{1-6}$alkoxy (—OR, where R is $C_{1-7}$alkyl, e.g., -Me, -Et, -nPr, -iPr, -nBu, -iBu, -tBu);

(5) acyl (—C(=O)R), including $C_{1-7}$alkyl-acyl (—C(=O)R, where R is $C_{1-7}$alkyl, e.g., -Me, -Et, -nPr, -iPr, -nBu, -iBu, -tBu); $C_{5-10}$aryl-acyl (—C(=O)R, where R is $C_{5-10}$aryl, e.g., phenyl, pyridyl, pyrrolyl, furanyl, thiofuranyl); $C_{5-10}$aryl-$C_{1-7}$alkyl-acyl (—C(=O)R, where R is $C_{5-10}$aryl-$C_{1-7}$alkyl, e.g., benzyl).

In one embodiment, Ar is substituted with, at least, one or more (e.g., 1, 2, 3, 4, etc.) groups selected from groups including those defined above in (1) through (5). (For example, Ar may also bear other substituents not listed above, e.g., $C_{1-6}$alkyl).

In one embodiment, Ar is phenyl or naphthyl (e.g., naphth-1-yl, naphth-2-yl).

In one embodiment, Ar is phenyl.

In one embodiment, Ar is naphthyl (e.g., naphth-1-yl, naphth-2-yl).

Some examples of such (non-polymeric) sensor molecules (SMs) include the following:

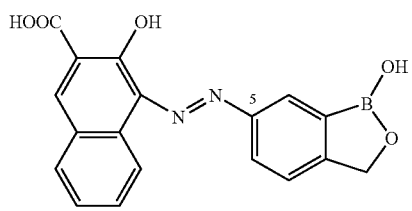

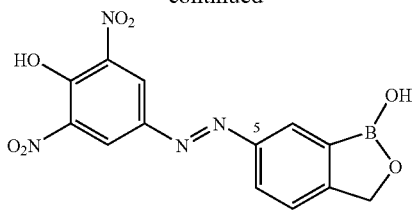

In one embodiment, LBL is, or incorporates, a fluorescence label (e.g., a fluorophore).

In one embodiment, the detectable label, LBL, is, or incorporates a sulphonamide, e.g., an aryl sulphonamide (i.e., —NHSO$_2$—R, where R is an aromatic organic group, for example, an aromatic organic group comprising 5 to 30 atoms selected from C, N, O, S, F, Cl, Br, and I).

Some examples of such (non-polymeric) sensor molecules (SMs) include the following:

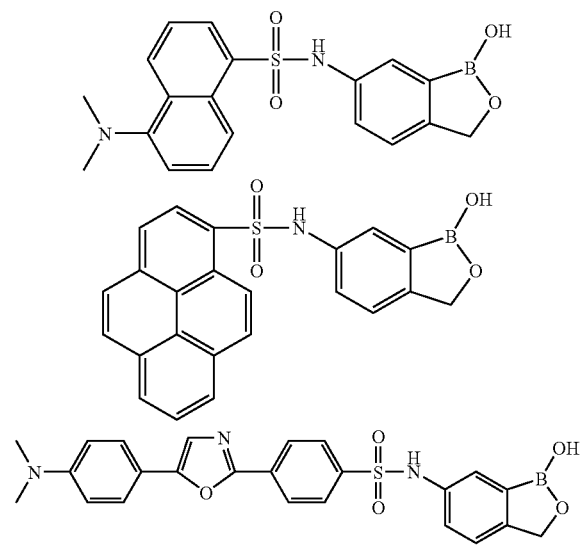

In one embodiment, LBL is, or incorporates, a redox label.

In one embodiment, the detectable label, LBL, is, or incorporates a ferrocene group, a group derived from Meldola's blue, or a quinone group.

In one embodiment, LBL is, or incorporates, a UV, visible, or infrared label.

In one embodiment, LBL is, or incorporates, an NMR label.

In one embodiment, LBL is, or incorporates, an electron spin resonance label.

In one embodiment (of the sensor molecules, per se), LBL as defined above, with the proviso that the compound is not: 3-hydroxy-4-(1-hydroxy-1,3-dihydro-benzo[c][1,2]oxaborol-6-ylazo)-naphthalene-2-carboxylic acid ("azoBOB").

Other sensor molecules (SMs) that incorporate the sensor group may also be prepared using well known methods.

Electrochemical Devices

One aspect of the invention pertains to a compound bearing a group suited to electrochemical conversion (e.g., a redox group), and useful, for example, in an electrochemical device.

In one embodiment, the compound has the following formula:

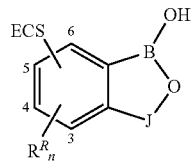

wherein:
J, n, each $R^R$, if present, and the ring attachment are as defined above for sensor groups; and
ECS is, or incorporates, a group suited to electrochemical conversion (e.g., a redox group).

An example of such a compound (which incorporates a ferrocene group) is:

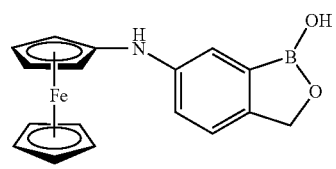

Uses

The compounds and polymers which incorporate a sensor group (SG) may be used in a range of methods for the (selective) detection and/or quantitation of alpha-hydroxy carboxylic acids, such as lactic acid/lactate. Many well known methods for detection and/or quantitation (e.g., determination, analysis, assay) may readily be adapted to permit the (selective) detection and/or quantitation of alpha-hydroxy carboxylic acids, such as lactic acid/lactate by employing the compounds and polymers described herein.

Thus, one aspect of the present invention pertains to a method for the (selective) detection of an alpha-hydroxy carboxylic acid, such as lactic acid/lactate, in a sample (preferably a fluid), comprising the steps of:
(a) contacting the sample with a compound or polymer that incorporates a sensor group (SG), as described herein;
(b) detecting and/or monitoring a chemical and/or physical property, or a change therein, of the resulting combination; and
(c) optionally correlating the chemical and/or physical property, or change therein, with the presence of and/or the amount of alpha-hydroxy carboxylic acid in the sample.

Holographic Uses

For example, polymers that incorporate a sensor group (SG) may be employed in holographic elements and holographic sensors useful for the (selective) detection and/or quantitation of alpha-hydroxy carboxylic acid, such as lactic acid/lactate. Methods for the manufacture and use of holographic elements and holographic sensors are well known in the art. See, for example, Lowe et al., WO 03/087899 A1, published 23 Oct. 2003; Lowe et al., WO 2004/081546 A1, published 23 Sep. 2004.

Thus, one aspect of the present invention pertains to a method for the preparation of a holographic element (e.g., that is useful for the (selective) detection of alpha-hydroxy carboxylic acid, such as lactic acid/lactate, e.g., in a fluid) comprising the steps of:
(a) disposing a polymerisable liquid on a substrate;
(b) polymerising the polymerisable liquid (e.g., by photopolymerisation) to form a medium comprising a polymer which incorporates a sensor group (SG), as described herein;

(c) disposing a holographic recording material within a part of (and preferably throughout) the volume of the medium;

(d) recording a holographic image (i.e., a hologram).

Another aspect of the present invention pertains to a holographic element (e.g., that is useful for the (selective) detection of alpha-hydroxy carboxylic acid, such as lactic acid/lactate, e.g., in a fluid) comprising:

(i) a medium (preferably disposed on a substrate) comprising a polymer which incorporates a sensor group (SG), as described herein, and (ii) a hologram disposed within a part of (and preferably throughout) the volume of the medium.

In use, an optical characteristic of the holographic element changes as a result of a variation of a physical property occurring within (and preferably throughout) the volume of the medium, wherein the variation arises as a result of interaction between the medium and alpha-hydroxy carboxylic acid, such as lactic acid/lactate. Preferably, the variation and the interaction are reversible.

The property of the holographic element which varies may be its charge density, volume, shape, density, viscosity, viscoelastic properties, strength, hardness, charge, hydrophobicity, swellability, integrity, cross-link density, or any other physical property. Variation of the, or each, physical property, in turn causes a variation of an optical characteristic, such as polarisability, reflectance, refractance, or absorbance of the holographic element.

Another aspect of the present invention pertains to a detection array, comprising an array of (e.g., discrete) sensors disposed on a substrate, each sensor comprising a holographic element as described herein.

Another aspect of the present invention pertains to a method for the (selective) detection of alpha-hydroxy carboxylic acid, such as lactic acid/lactate, in a fluid, comprising the steps of:

(a) contacting the fluid with a holographic element comprising:

(i) a medium (preferably disposed on a substrate) comprising a polymer which incorporates a sensor group (SG), as described herein, and (ii) a hologram disposed within a part of (and preferably throughout) the volume of the medium;

(b) detecting and/or monitoring an optical characteristic of the holographic element and/or changes in an optical characteristic of the holographic element; and (c) optionally correlating the optical characteristic, or change therein, with the presence of and/or the amount of alpha-hydroxy carboxylic acid, such as lactic acid/lactate, in the fluid.

Assays

Similarly, sensor molecules (SMs) that incorporate a sensor group (SG), as described herein, may be employed in (e.g., solution based) methods for the (selective) detection and/or quantitation of alpha-hydroxy carboxylic acids, such as lactic acid/lactate (e.g., "assays," "assay methods").

For example, such sensor molecules (SMs) may be used in solution as free complexing agents for alpha-hydroxy carboxylic acids, such as lactic acid/lactate, to give detectable and/or quantifiable spectrophotometric, fluorescence, electrochemical, etc. responses. Such sensor molecules (SMs) may also be used in other non-solution methods (e.g., employing gels, solid films, holography, etc.).

Thus, one aspect of the present invention pertains to assay methods for detecting, and preferably quantifying, an analyte of interest (i.e., alpha-hydroxy carboxylic acids, such as lactic acid/lactate) which is present in a sample composition. The terms "assay" and "assay method," as used herein, pertain to a method of detecting the presence of (e.g., qualitative assay), and preferably quantifying (e.g., quantitative assays), an analyte of interest (e.g., alpha-hydroxy carboxylic acids, such as lactic acid/lactate).

Assays of the present invention generally involve contacting alpha-hydroxy carboxylic acid, such as lactic acid/lactate (which is typically one component of a sample composition) with a pre-determined non-limiting amount of one or more assay reagents ((e.g., non-polymeric) sensor molecules (SMs)), measuring an indicative property of a resulting product, and correlating the measured indicative property with the amount of alpha-hydroxy carboxylic acid, such as lactic acid/lactate, present in the original sample, typically by using a relationship determined from standard samples containing known amounts of alpha-hydroxy carboxylic acid, such as lactic acid/lactate, in the range expected for the sample to be tested.

In a qualitative assay, simply determining whether the measured indicative property is above or below a threshold value (established, for example, using samples known to contain or be free of lactate) may be sufficient to establish the assay result. Thus, unless otherwise required, the term "measuring" can refer to either qualitative or quantitative determination.

The terms "sample" and "sample composition," as used herein, pertain to a composition which comprises alpha-hydroxy carboxylic acid, such as lactic acid/lactate, or which may be processed to comprise such compounds. The sample may be in solid, emulsion, suspension, liquid, or gas form. Typically, the sample is processed (e.g., by the addition of a liquid) so as to be a fluid (i.e., free flowing) form (e.g., emulsion, suspension, solution) in order to readily permit and simplify the detection and quantification of alpha-hydroxy carboxylic acid, such as lactic acid/lactate using conventional methods.

Thus, one aspect of the present invention pertains to a method for the (selective) detection of alpha-hydroxy carboxylic acid, such as lactic acid/lactate, in a sample, comprising the steps of:

(a) contacting the sample with a compound or polymer that incorporates a sensor group (SG), as described herein, e.g., in solution;

(b) detecting and/or monitoring a chemical and/or physical property, or a change therein, of the resulting combination; and (c) optionally correlating the chemical and/or physical property, or change therein, with the presence of and/or the amount of alpha-hydroxy carboxylic acid, such as lactic acid/lactate, in the sample.

In practice, the contacting step may be performed in one of a number of ways. For example, a sample solution may be added to a solution of the sensor molecule; or a solid sample may be added to a solution of the sensor molecule; or a portion of solid sensor molecule may be added to a sample solution; etc.

The compound that incorporates a sensor group (SG) may be, for example, non-polymeric or polymeric. For example, the sensor group (SG) may be attached to a soluble polymer (e.g., a water soluble polymer).

In one embodiment, the chemical and/or physical property is colour, or a change in colour (e.g., as judged by the human eye or a calorimeter).

In one embodiment, the chemical and/or physical property is absorbance (or transmittance or reflectance or refractance) at one or more UV or visible wavelengths (e.g., 350 to 700 nm).

In one embodiment, the chemical and/or physical property is fluorescence.

In one embodiment, the chemical and/or physical property is the chemical shift of the boron atom of the sensor group (e.g., as determined using $^{11}$B NMR).

In one embodiment, the chemical and/or physical property is the field strength of an electron spin resonance peak (e.g., as determined using electron spin resonance spectroscopy).

The present invention also provides reagents, reagent mixtures, reagent sets comprising one or more separate reagents, and reagent kits (e.g., test kits) comprising one or more reagents, reagent mixtures, and reagent sets in packaged combination, all for use in the assay methods of the present invention. Reagents, reagent mixtures, and/or sets of reagents for use in the assays of the present invention are typically provided in one or more suitable containers or devices. Each reagent may be in a separate container or various reagents can be combined in one or more containers (e.g., as a reagent mixture), depending on the compatibility (e.g., cross-reactivity) and stability of the reagents. Reagents (or reagent mixtures) may be in solid (e.g., lyophilised), liquid, or gaseous form, though typically are in solid or liquid form.

Reagents, reagent mixtures, and/or reagent sets are typically presented in a commercially packaged form as a reagent kit; for example, as a packaged combination of one or more containers, devices, or the like holding one or more reagents or reagent mixtures, and usually including written instructions for the performance of the assays. Reagent kits may also include materials (e.g., reagents, standards, etc.) for calibration and control purposes.

Reagents and reagent mixtures may further comprise one or more ancillary materials, including, but not limited to, buffers, surfactants (e.g., non-ionic surfactants), stabilisers, preservatives, and the like.

Applications

The methods and materials described herein for use in the (selective) detection and/or quantitation of alpha-hydroxy carboxylic acids, such as lactic acid/lactate, are useful in a wide range of applications.

For example, monitoring of blood lactate levels is particularly useful in sport's medicine, because lactate is the unique metabolic marker indicative of the capability of the muscles for athletic performance.

Also, blood lactate levels can be used in clinical diagnostics, for example, to diagnose and predict multiple organ failure and death in patients with septic shock, and to predict the function of newly transplanted livers.

Lactate levels can also be used a measure of metabolism, for example, in cell cultures. For example, cell cultures usually respond to up- and down-regulation of genes and to external stimuli such as biopharmaceuticals with a shift in metabolism, often reflect in a change in the cells external environment. This shift in metabolism can usually be observed by monitoring changes in lactate levels.

Lactate analysis is also important in the food industry. For example, lactate influences the flavour, stability and quality of many foods, and so lactate analysis is useful in the quality control of foodstuffs, including wine, cider, beer, and milk. Detection of lactate can often be used to indicate early contamination of such products.

Lactate is also important in opthalmology, and in particular in connection with contact lenses and associated ocular disorders. For example, contact lenses incorporating a sensor polymer (SP) or a sensor molecule (SM) which changes colour (e.g., from colourless to coloured) on detection of (appreciable levels on lactate would be useful in the early detection of ocular conditions or disorders.

EXAMPLES

The following are examples are provided solely to illustrate the present invention and are not intended to limit the scope of the invention, as described herein.

Example 1

Synthesis of BOBA

N-(1-Hydroxy-1,3-dihydro-benzo[c][1,2]oxaborol-6-yl)-acrylamide

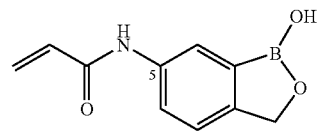

A solution of 5A2HMPBA (0.5 g, 0.0027 mol) in 3 mL water was cooled in an ice bath. A solution of sodium hydroxide (0.2 g in 2 mL, 0.0054 mol) was added. The resulting pH was ~8. Acryloyl chloride (0.5 mL, 0.0054 mol) was added dropwise (a white precipitate formed immediately) over a period of 5 minutes. The mixture was then left to stir while monitoring the pH (ideally the pH should be maintained between pH 7 and 9). No change in pH was observed. The mixture was allowed to stand overnight while warming to room temperature. The grey precipitate was filtered off and washed with cold water. The product was allowed to dry under high vacuum line over $P_2O_5$.

Example 2

Synthesis of a 10% BOBA Polyacrylamide Polymer

A 10 mol % BOBA polyacrylamide polymer was prepared from the following monomers:

| Monomer | mol. wt. | mg | mmol | mole % |
| --- | --- | --- | --- | --- |
| acrylamide | 71.08 | 92.59 | 1.303 | ~88.19 |
| N,N'-methylenebis(acrylamide) | 154.17 | 3.93 | 0.0255 | ~1.73 |
| BOBA | 203.00 | 30.28 | 0.149 | ~10.08 |

The monomers were dissolved in 250 μL of solution of 2% (w/v) 2-dimethoxy-2-phenyl acetophenone (DMPA) in dimethylsulfoxide (DMSO). A 100 μL aliquot of this mixture was pipetted onto the polyester surface of an aluminised polyester sheet set on a glass plate. A glass microscope slide, which had been treated with 3-(trimethoxysilyl)-propyl methacrylate, was then placed, silane-treated side down, onto the monomer mixture. The films were polymerised by UV initiated free radical reaction at 20° C. for approximately 1 hour (~350 nm; UV exposure unit, Model No. 555-279, RS components, UK). The polymerised films were pealed off the aluminised polyester sheet while immersed in deionised water. The slides were left to dry, polymer side up, before use in the preparation of the holographic element.

Example 3

Preparation of a (Silverless) Holographic Element Employing BOBA Polymer

A silverless holographic element was prepared by forming a second polymer (P2) "within" the 10 mol % BOBA polyacrylamide polymer. The following liquid mixture (EXL 2 solution) was prepared from the following materials:

| | |
|---|---|
| 2-dimethoxy-2-phenyl acetophenone (DMPA) | 5 mg |
| Irgacure 2959 | 5 mg |
| 1,4-bis(acryloyl)piperazine (BAP) | 0.4 g |
| diethylene glycol (DIGOL) | 1000 µL |
| deionised water | 4 ml |
| triethylamine (TEA) | 40 µL |
| 2% ascorbic acid | 100 µL |

(Irgacure 2959 is 1-[4-(2-hydroxyethoxy)-phenyl]-2-hydroxy-2-methyl-1-propane-1-one, a highly efficient non-yellowing radical photoinitiator for UV curing systems.)

The 10 mol % BOBA polyacrylamide polymer films were placed "face-down" onto 400 µL of the EXL 2 solution and allowed to stand for 30 minutes, absorbing the liquid. Excess solution was wiped off with a rubber wiper blade and the slide was allowed to dry, polymer "face-up", under a fan for 3 hours.

Holograms were then formed within the polymer films. Under green lighting, the UV laser was left to warm up for 20 minutes and the slide left in position ready to shoot (polymer side down) for this time. (Unlike when shooting silver holograms, only sections of the slide are exposed to the UV light when the laser is triggered.) Slides were "shot" with 1, 2, 3, or 5 pulses or a Kodak exposure using a tripled Nd:YAG laser (355 nm, Brilliant B, Quantel), and then allowed to soak in distilled water for 30 minutes. Holograms were analysed using a LOT-ORIEL MS127i model 77480 imaging spectrograph in single channel mode with a 256×1024-pixel InstaSpec IV CCD detector and processing software, for example, as described in Mayes et al., 1998, *Journal of Molecular Recognition*, Vol. 11, pp. 168-174. It was found that "shooting" with 3 pulses yielded the best hologram.

The piece of the slide containing the "3 shots" hologram was cut from the whole slide (~8 mm wide) and placed in a 4 mL plastic cuvette with the polymer side facing inward. Phosphate buffered saline buffer (PBS, 1 mL, pH 7.4, ionic strength of 154 mM, concentration of 200 mM) was added, the cuvette was covered and left to stir overnight at 30° C. to allow the system to reach equilibrium.

A 0.1 M solution of sodium lactate in PBS buffer was prepared. Peak wavelength (nm) was measured over time, as 20 µL aliquots of 0.1 M lactate solution were added to the cuvette at regular time intervals (the system was allowed to equilibrate between additions). After six additions, the holographic element was removed from the cuvette and washed with PBS buffer (2×1 mL) and then left to stabilise again with fresh PBS buffer (1 mL). The peak wavelength was found to return almost to the original baseline value. The data demonstrate that the changes within the holographic element are fully reversible.

Figure 2:
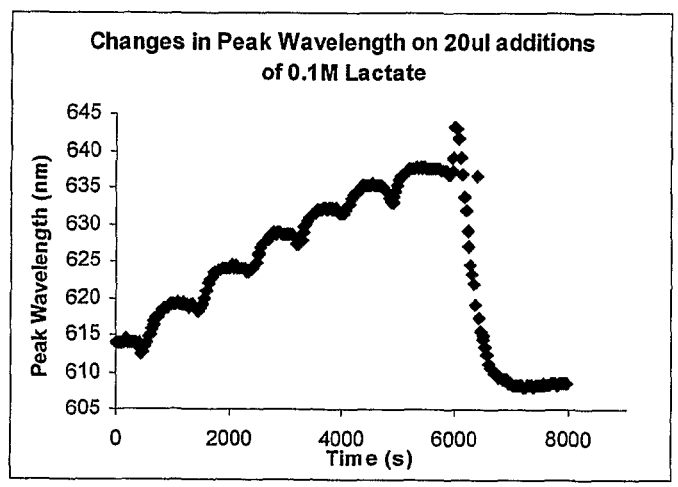
FIG. 2 is a graph of peak wavelength (nm) versus time (s), for a holographic sensor prepared from a 10% BOBA polymer, as 20 μL aliquots of 0.1 M lactate solution was applied at regular intervals. After six iterations, the holographic sensor was washed with phosphate buffered saline (PBS).

FIG. 2 is a graph of peak wavelength (nm) versus time (s), for a holographic element prepared from a 10% BOBA polymer, as 20 µL aliquots of 0.1 M lactate solution was applied at regular intervals. After six iterations, the holographic element was washed with phosphate buffered saline (PBS).

Figure 3:
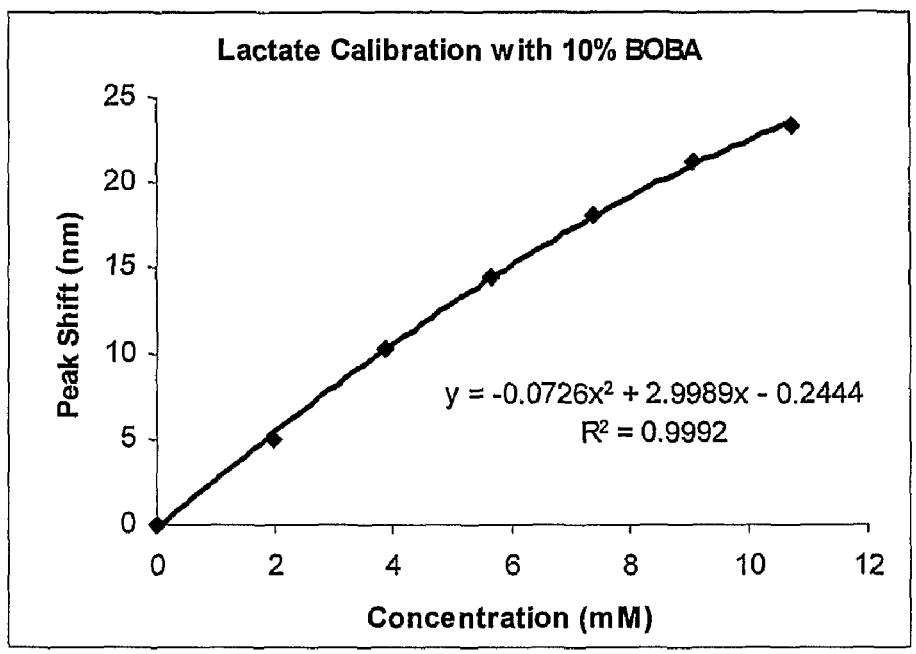
FIG. 3 is a graph of peak shift (nm) versus accumulated concentration of lactate (mM) and shows an approximately linear relationship.

FIG. 3 is a graph of peak shift (nm) versus accumulated concentration of lactate (mM) and shows an approximately linear relationship.

The same holographic element was then tested for its response to glucose following the same method as described above for lactose, except that a final wash was not performed.

Figure 4:
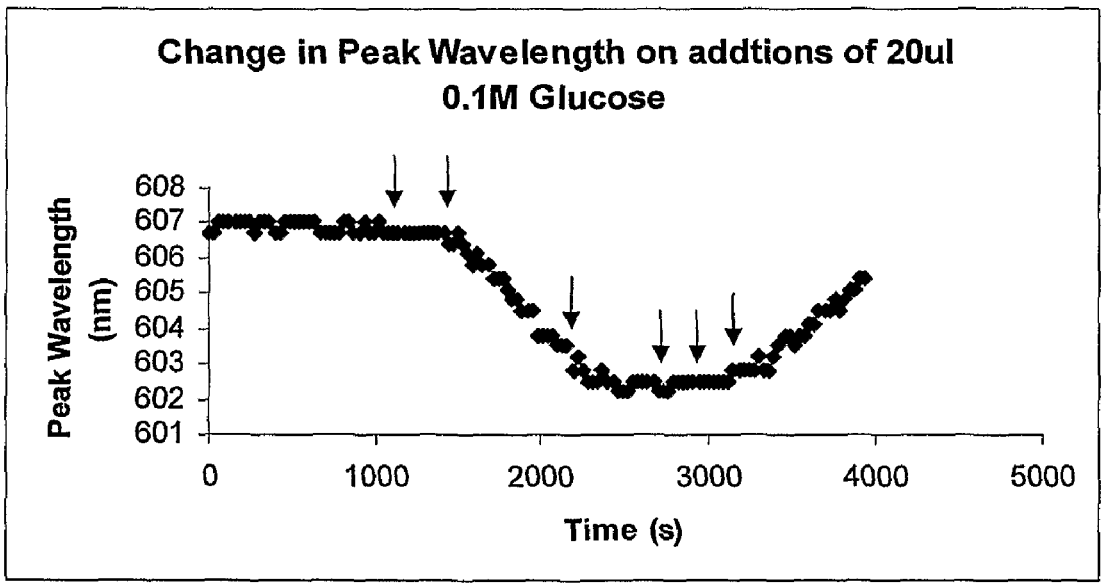
FIG. 4 is a graph of peak wavelength (nm) versus time (s), for the same holographic sensor, as 20 μL aliquots of 0.1 M glucose solution were applied (the arrows indicate the application of glucose).

FIG. 4 is a graph of peak wavelength (nm) versus time (s), for the same holographic element, as 20 µL aliquots of 0.1 M glucose solution were applied (the arrows indicate the application of glucose).

No change in peak wavelength was observed following the first application of glucose. Although subsequent additions did give rise to a small and irregular change (the entire range for 6 applications of glucose is only about 5 nm, compared to 25 nm for lactate), it is believed that this represents "noise" in the non-optimized device.

Example 4

Synthesis of Axo-BOB: 3-hydroxy-4-(1-hydroxy-1,3,-dihydrobenzo[c][1,2]oxaboral-6-yl-azo)-naphthalene-2-carboxylic acid

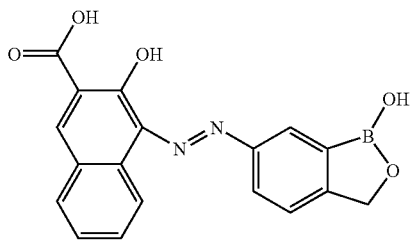

A similar method is described in Lennarz et al., *Journal of American Chemical Society*, 1960, Vol. 82, pp. 2172-2175.

(Diazotization) A solution of 0.5 g (0.0027 mol) of 5A2HMPBA in 3 mL water was cooled in an ice bath. Approximately 60 µL of concentrated HCl was added to the solution, and the solution stirred well and cooled to 0-5° C. A solution of $NaNO_2$ (0.1896 g, 0.0027 mol, in 1.5 mL water) was added at such a rate that the temperature did not exceed 5° C. Near the end of the addition, the suspension was tested for excess of the nitrite ion with starch iodide paper. When almost all of the solution had been added the test was positive (a dark spot was seen). A further ~5 mg of 5A2HMPBA were added to give a negative test result. The suspension was then stirred for 10 minutes.

(Coupling) The suspension of diazotized 5A2HMPBA was added to a cool stirred solution of 3-hydroxy-2-naphthoic acid (0.507 g, 0.0027 mole, in 4.5 mL of 10% NaOH) and stirred for 30 minutes. 5 mL 10% HCl and 2 mL of water was added to produce a deep red-coloured precipitate. The mixture was refrigerated overnight and, the following day, the precipitate was filtered and allowed to dry under high vacuum line over $P_2O_5$.

Figure 5:
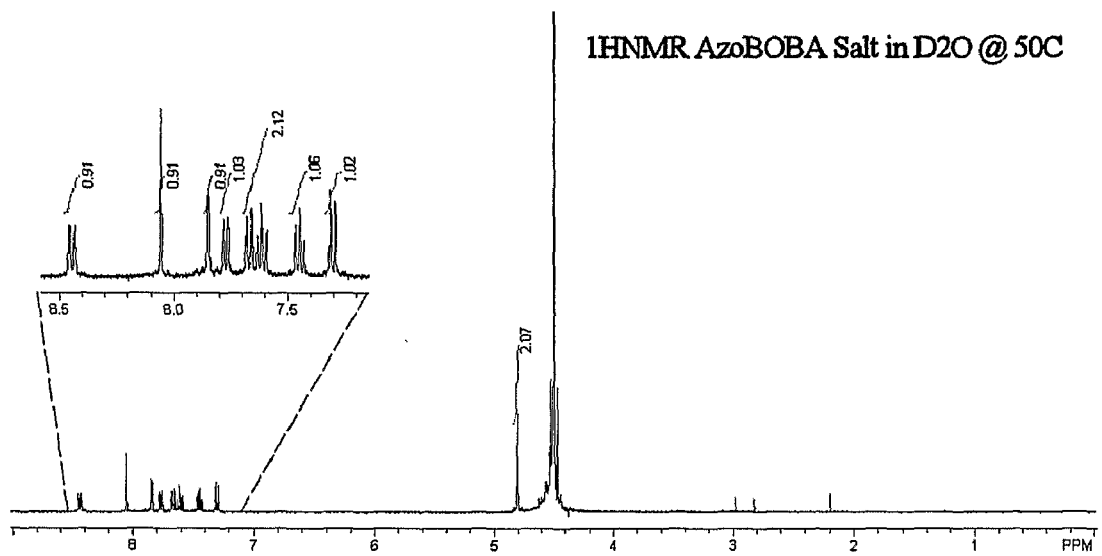
FIG. 5 shows the $^1$H NMR (400 MHz) spectrum for azo-BOB sodium salt.

FIG. 5 shows the $^1H$ NMR (Joel JNM-LA 400 MHz) spectrum for the resulting azo-BOB sodium salt.

Figure 6:
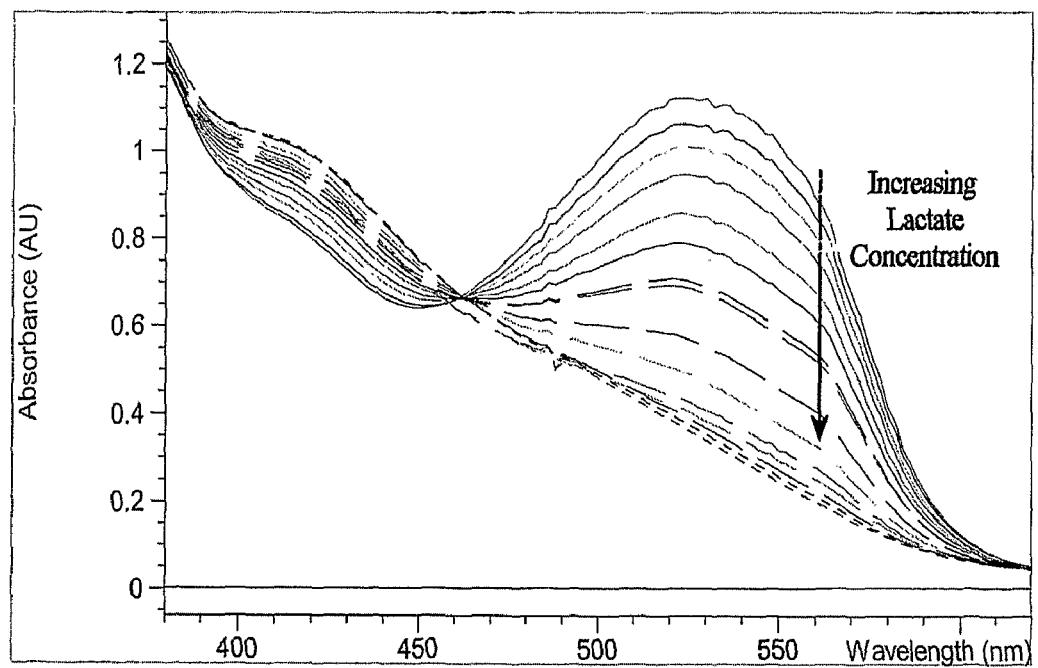
FIG. 6 shows the UV spectra recorded for 0.2585 mM solutions of azo-BOB in dimethylformamide (DMF) with increasing (from 0 to 0.48 mM) lactate concentration.

FIG. 6 shows the UV spectra (Hewlett Packard 8452A Diode Array UV Spectrometer) recorded for 0.2585 mM solutions of azo-BOB in dimethylformamide (DMF) with increasing (from 0 to 0.48 mM) lactate concentration.

The data extracted from the UV spectra are summarised below.

| Conc. (mM) Azo-BOB | Conc. (mM) Lactate | Molar Ratio (Lactate/ Azo-BOB) | Absorbance 530 nm | Absorbance 420 nm |
|---|---|---|---|---|
| 0.2585 | 0 | 0 | 1.1216 | 0.789 |
| 0.2585 | 0.0080 | 0.0311 | 1.0612 | 0.81139 |
| 0.2585 | 0.0316 | 0.1221 | 1.0072 | 0.83818 |
| 0.2585 | 0.0542 | 0.2097 | 0.94093 | 0.85666 |
| 0.2585 | 0.0760 | 0.2940 | 0.84938 | 0.8811 |
| 0.2585 | 0.0970 | 0.3752 | 0.77922 | 0.89758 |
| 0.2585 | 0.1172 | 0.4535 | 0.69202 | 0.91476 |
| 0.2585 | 0.1368 | 0.5291 | 0.6748 | 0.92664 |
| 0.2585 | 0.1739 | 0.6726 | 0.55365 | 0.95168 |
| 0.2585 | 0.2085 | 0.8067 | 0.47182 | 0.96548 |
| 0.2585 | 0.2410 | 0.9322 | 0.40703 | 0.93419 |
| 0.2585 | 0.2715 | 1.0501 | 0.383 | 0.94124 |
| 0.2585 | 0.3271 | 1.2653 | 0.36787 | 0.98666 |
| 0.2585 | 0.3766 | 1.4569 | 0.35359 | 0.98979 |
| 0.2585 | 0.4795 | 1.8551 | 0.33965 | 0.99318 |

Figure 7:
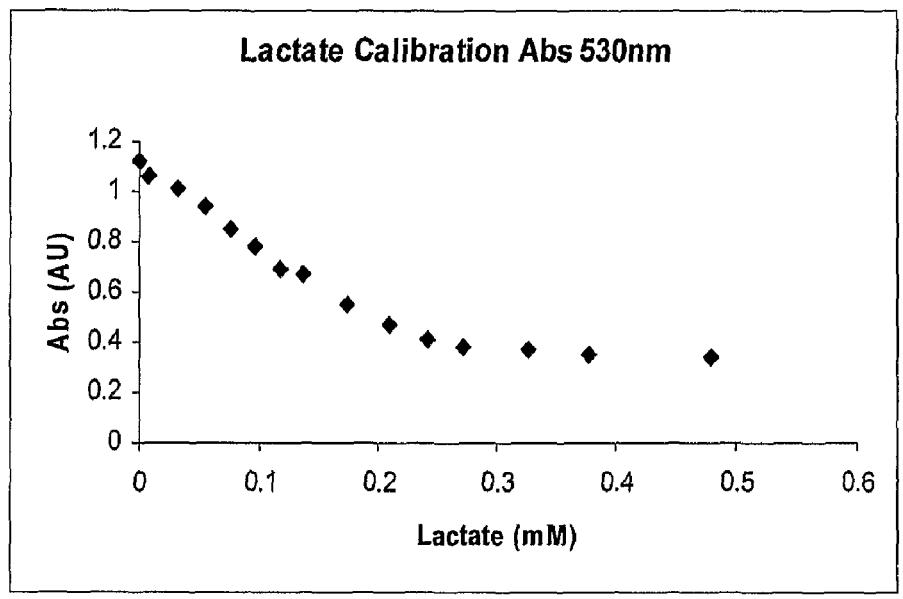
FIG. 7 is a graph of UV absorbance at 530 nm as a function of lactate concentration (mM). An approximately linear relationship is evident for concentrations up to about 0.25 mM.

FIG. 7 is a graph of UV absorbance at 530 nm as a function of lactate concentration (mM). An approximately linear relationship is evident for concentrations up to about 0.25 mM.

Figure 8:
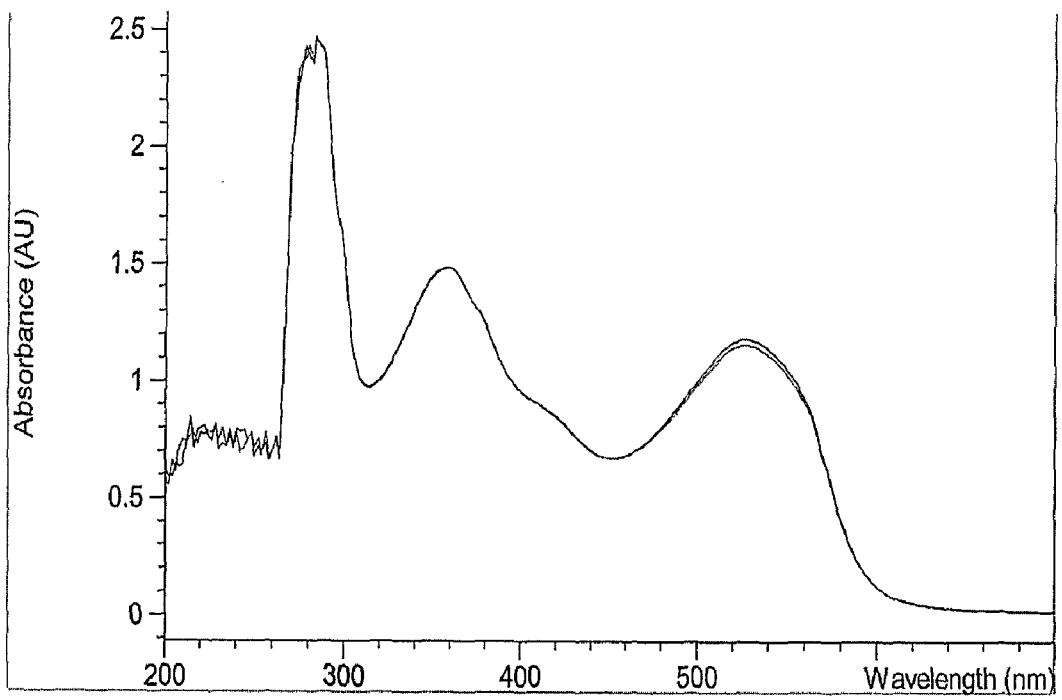
FIG. 8 show the UV spectra recorded for 0.2585 mM solutions of azo-BOB in dimethylformamide (DMF) with ~0.6 mM glucose, and without glucose.

FIG. 8 show the UV spectra (Hewlett Packard 8452A Diode Array UV Spectrometer) recorded for 0.2585 mM solutions of azo-BOB in dimethylformamide (DMF) with ~0.6 mM glucose, and without glucose.

The UV spectrum changes very little upon addition of glucose, again indicating that glucose does not bind to azo-BOB. The absorbance at 530 nm was 1.174 (without glucose) and 1.147 (with glucose). The absorbance at 420 nm was 0.84267 (without glucose) and 0.84705 (with glucose).

Additionally, a very evident colour change, from red to yellow, was observed upon addition of lactate to the solution of azo-BOB in DMF. In contrast, no colour change was observed upon addition of glucose.

Figure 9:
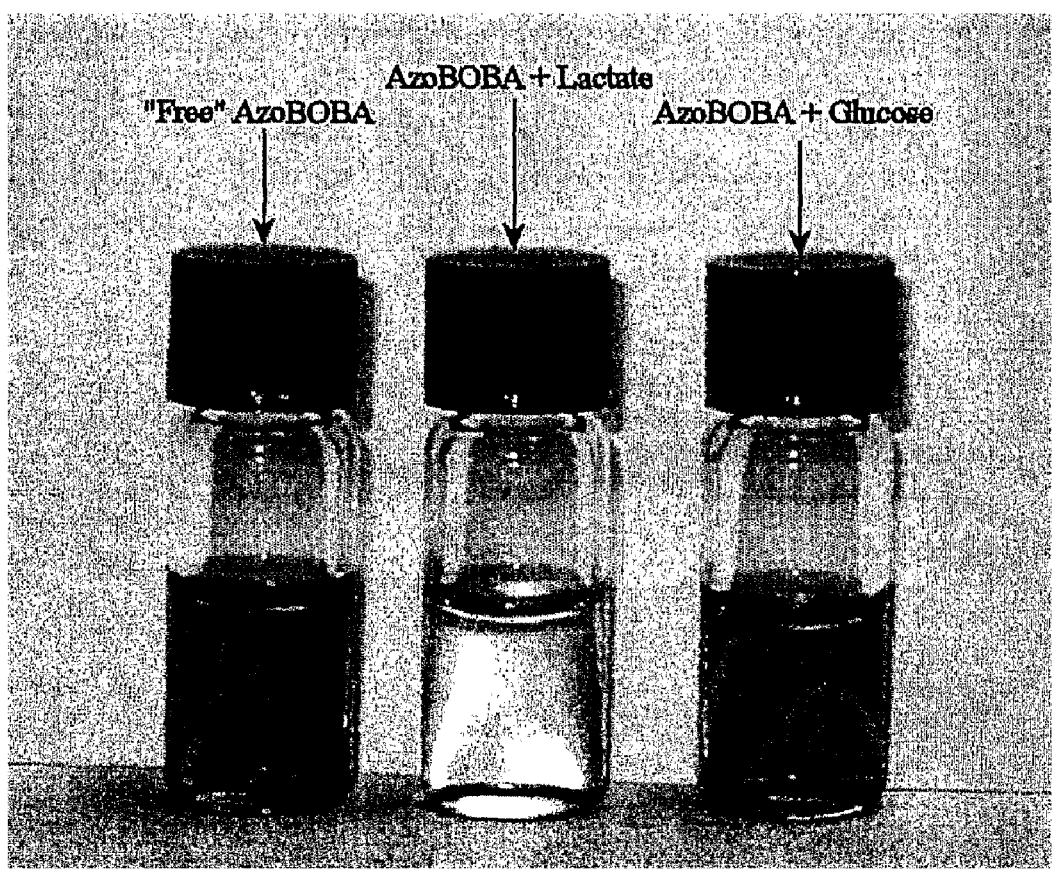
FIG. 9 is a photograph showing solutions of "free" azo-BOB (red), azo-BOB with lactate (pale yellow), and azo-BOB with glucose (red).

FIG. 9 is a photograph showing solutions of "free" azo-BOB (red), azo-BOB with lactate (pale yellow), and azo-BOB with glucose (red).

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the spirit and scope of the present invention.

The present invention is not limited to those embodiments which are encompassed by the appended claims, which claims pertain to only some of many preferred embodiments.

The invention claimed is:

1. A holographic element comprising:
(i) a medium comprising a sensor polymer which incorporates a sensor group of the following formula:

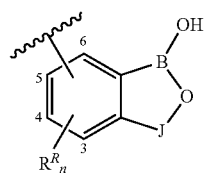

wherein:
J is independently —$CH_2$— or —$CH_2CH_2$—;
n is independently 0, 1, 2, or 3;
each $R^R$ is independently a ring substituent selected from $C_{1-6}$alkoxy, —$NO_2$, $C_{1-7}$alkyl-acyl, $C_{5-10}$aryl-acyl, $C_{5-10}$aryl-$C_{1-7}$alkyl-acyl, —OH, —COOH, —F, —Cl, —Br, —I, and —CN; and
the ring attachment is via the 3-, 4-, 5-, or 6-ring position; and
(ii) a hologram disposed within a part of the volume of the medium;
wherein the hologram is:
a "phase" hologram comprising a 3-dimensional distribution (modulation) of refractive index wherein the distribution is a physical record of an original interference pattern; and/or
an "amplitude" hologram comprising a 3-dimensional distribution (modulation) of a radiation-absorbing material, wherein the distribution is a physical record of an original interference pattern.

2. A holographic element according to claim 1, wherein J is —$CH_2$—.

3. A holographic element according to claim 1, wherein J is —$CH_2CH_2$—.

4. A holographic element according to claim 1, wherein n is 0.

5. A holographic element according to claim 1, wherein n is 1.

6. A holographic element according to claim 1, wherein n is 2.

7. A holographic element according to claim 1, wherein the ring attachment is via the 3-, 4-, or 5-ring position.

8. A holographic element according to claim 1, wherein the ring attachment is via the 5-ring position.

9. A holographic element according to claim 1, wherein the sensor polymer is a non-vinyl polymer.

10. A holographic element according to claim 1, wherein the sensor polymer is selected from: gelatin; K-carageenan; agar; agarose; polyvinyl alcohol; a sol-gel; a hydro-gel; a polysaccharide; a protein; an oligonucleotide; RNA; DNA; cellulose; cellulose acetate; a siloxane; and a polyimide.

11. A detection array comprising an array of sensors disposed on a substrate, each sensor comprising a holographic element according to claim 1.

12. A holographic element according to claim 1, wherein J is independently —$CH_2$—; n is independently 0; and the ring attachment is via the 5-ring position.

13. A detection array comprising an array of sensors disposed on a substrate, each sensor comprising a holographic element according to claim 12.

14. A holographic element according to claim 1, wherein said sensor polymer incorporates two or more identical sensor groups of the recited formula.

15. A detection array comprising an array of sensors disposed on a substrate, each sensor comprising a holographic element according to claim 14.

16. A holographic element according to claim 1, wherein the sensor polymer is selected from: polyether, polyester, polycarbonate, polyamide, polyurea, polyurethane, and copolymers thereof.

17. A detection array comprising an array of sensors disposed on a substrate, each sensor comprising a holographic element according to claim 16.

18. A holographic element according to claim 1, wherein the sensor polymer is a vinyl polymer.

19. A detection array comprising an array of sensors disposed on a substrate, each sensor comprising a holographic element according to claim 18.

20. A holographic element according to claim 1, wherein the sensor polymer is selected from: poly(alkylene); poly (arylalklene); poly(acrylic acid); poly($C_{1-4}$alkyl substituted acrylic acid); poly($C_{1-4}$alkyl acrylate); poly($C_{1-4}$alkyl $C_{1-4}$alkyl-substituted acrylate); poly(hydroxy-$C_{1-4}$alkyl acrylate); poly(hydroxy-$C_{1-4}$alkyl $C_{1-4}$alkyl-substituted acrylate); poly(acrylamide); poly($C_{1-4}$alkyl substituted acrylamide); poly(N—$C_{1-4}$alkyl-substituted acrylamide); poly(N,N-di-$C_1$alkyl-substituted acrylamide); poly(N—$C_{1-4}$-alkyl-substituted $C_{1-4}$-alkyl substituted acrylamide); poly(N,N-di-$C_1$alkyl-substituted $C_{1-4}$alkyl substituted acrylamide); poly(vinyl ester); poly($C_{1-4}$-alkyl substituted vinyl ester); poly(acrylonitrile); poly($C_{1-4}$-alkyl substituted acrylonitrile); poly(vinyl chloride); poly($C_{1-4}$-alkyl substituted vinyl chloride); and copolymers thereof.

21. A detection array comprising an array of sensors disposed on a substrate, each sensor comprising a holographic element according to claim 20.

22. A holographic element according to claim 1, wherein the sensor polymer is selected from: polyethylene; polypropylene; polybutylene; polyisobutylene; polyisoprene; polystyrene; poly(acrylic acid); poly(methacrylic acid); poly(methyl acrylate); poly(methyl methacrylate); poly(hydroxyethyl acrylate); poly(hydroxyethyl methacrylate); poly(acrylamide); poly(methacrylamide); poly(N-methyl-acrylamide); poly(N-methyl-methacrylamide); poly(vinyl acetate); poly(methylvinyl acetate); poly(acrylonitrile); poly(methacrylonitrile); poly(vinyl chloride); poly(methylvinyl chloride); and copolymers thereof.

23. A detection array comprising an array of sensors disposed on a substrate, each sensor comprising a holographic element according to claim 22.

24. A holographic element according to claim 1, wherein said sensor polymer is prepared by polymerisation of acrylamide and N-(1-hydroxy-1,3-dihydro-benzo[c][1,2]oxaborol-6-yl)-acrylamide.

25. A detection array comprising an array of sensors disposed on a substrate, each sensor comprising a holographic element according to claim 24.

26. A holographic element according to claim 1, wherein said sensor polymer is prepared by polymerisation of acrylamide, N-(1-hydroxy-1,3-dihydro-benzo[c][1,2]oxaborol-6-yl)-acrylamide, and N,N'-methylenebis(acrylamide).

27. A detection array comprising an array of sensors disposed on a substrate, each sensor comprising a holographic element according to claim 26.

28. A holographic element according to claim 1, wherein the sensor polymer comprises a monomer unit bearing said sensor group.

29. A holographic element according to claim 28, wherein said sensor group is attached to said monomer unit directly or via a linker group.

30. A holographic element according to claim 29, wherein said linker group is selected from: $C_{1-6}$alkylene; oxy; amino; substituted amino; amino acyl; acyl amino; N-substituted amino acyl; N-substituted acyl amino; ester; reverse ester; urea; substituted urea; carbamate; reverse carbamate; N-substituted carbamate; N-substituted reverse carbamate; and combinations thereof.

31. A holographic element according to claim 28, wherein said monomer unit is a non-vinyl monomer.

32. A holographic element according to claim 28, wherein said monomer unit is a vinyl monomer selected from: $C_{1-6}$alkenylene; $C_{5-10}$aryl-$C_{1-6}$alkenylene; acrylic acid; $C_{1-4}$-alkyl substituted acrylic acid; $C_{1-4}$alkyl acrylate; $C_{1-4}$alkyl $C_{1-4}$alkyl-substituted acrylate; hydroxyl-$C_{1-4}$-alkyl acrylate; hydroxyl-$C_{1-4}$alkyl $C_{1-4}$alkyl-substituted acrylate; acrylamide; $C_{1-4}$alkyl substituted acrylamide; N—$C_{1-4}$-alkyl-substituted acrylamide; N,N-di-$C_{1-4}$alkyl-substituted acrylamide; N—$C_{1-4}$-alkyl-substituted $C_{1-4}$alkyl substituted acrylamide; N,N-di-$C_{1-4}$alkyl-substituted $C_{1-4}$alkyl substituted acrylamide; vinyl ester; $C_{1-4}$alkyl substituted vinyl ester; poly(acrylonitrile); $C_{1-4}$alkyl substituted acrylonitrile; vinyl chloride; and $C_{1-4}$alkyl substituted vinyl chloride.

33. A holographic element according to claim 28, wherein said monomer unit is a vinyl monomer selected from: ethylene; propylene; butylene; isobutylene; isoprene; styrene; acrylic acid; methacrylic acid; methyl acrylate; methyl methacrylate; hydroxyethyl acrylate; hydroxyethyl methacrylate; acrylamide; methacrylamide; N-methyl-acrylamide; N-methyl-methacrylamide; vinyl acetate; methylvinyl acetate; acrylonitrile; methacrylonitrile; vinyl chloride; and methylvinyl chloride.

34. A holographic element according to claim 28, wherein said monomer unit is a vinyl monomer selected from: acrylic acid; $C_{1-4}$alkyl substituted acrylic acid; $C_{1-4}$-alkyl acrylate; $C_{1-4}$alkyl $C_{1-4}$alkyl-substituted acrylate; hydroxyl-$C_{1-4}$-alkyl acrylate; hydroxyl-$C_{1-4}$alkyl $C_{1-4}$alkyl-substituted acrylate; acrylamide; $C_{1-4}$alkyl substituted acrylamide; N—$C_{1-4}$-alkyl-substituted acrylamide; N,N-di-$C_{1-4}$alkyl-substituted acrylamide; N—$C_{1-4}$-alkyl-substituted $C_{1-4}$alkyl substituted acrylamide; and N,N-di-$C_{1-4}$alkyl-substituted $C_{1-4}$alkyl substituted acrylamide.

35. A holographic element according to claim 28, wherein said monomer unit is a vinyl monomer selected from: acrylic acid; methacrylic acid; methyl acrylate; methyl methacrylate; hydroxyethyl acrylate; hydroxyethyl methacrylate; acrylamide; methacrylamide; N-methyl-acrylamide; and N-methyl-methacrylamide.

36. A holographic element according to claim 28, wherein said monomer unit is a vinyl monomer selected from: acrylamide; $C_{1-4}$alkyl substituted acrylamide; N—$C_{1-4}$-alkyl-substituted acrylamide; N,N-di-$C_{1-4}$alkyl-substituted acrylamide; N—$C_{1-4}$-alkyl-substituted $C_{1-4}$alkyl substituted acrylamide; and N,N-di-$C_{1-4}$alkyl-substituted $C_{1-4}$alkyl substituted acrylamide.

37. A holographic element according to claim 28, wherein said monomer unit is a vinyl monomer selected from: acrylamide; methacrylamide; N-methyl-acrylamide; and N-methyl-methacrylamide.

38. A holographic element according to claim 28, wherein said monomer unit is a vinyl monomer selected from: acrylamide and $C_{1-4}$alkyl substituted acrylamide.

39. A holographic element according to claim 28, wherein said monomer unit is a vinyl monomer selected from: acrylamide and methacrylamide.

40. A holographic element according to claim 28, wherein said monomer unit is acrylamide.

41. A holographic element according to claim 28, wherein said monomer unit is N-substituted acrylamide or N-substituted $C_{1-4}$alkyl substituted acrylamide which bears said sensor group as an N-substituent.

42. A detection array comprising an array of sensors disposed on a substrate, each sensor comprising a holographic element according to claim 28.

43. A holographic element according to claim 28, wherein said monomer unit is a vinyl monomer.

44. A detection array comprising an array of sensors disposed on a substrate, each sensor comprising a holographic element according to claim 43.

* * * * *